US008034343B2

(12) United States Patent
Parnet et al.

(10) Patent No.: US 8,034,343 B2
(45) Date of Patent: *Oct. 11, 2011

(54) METHODS OF TREATING INFLAMMATORY DISORDERS OF THE LUNGS

(75) Inventors: Patricia Parnet, Bordeaux (FR); John E. Sims, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/604,289

(22) Filed: Oct. 22, 2009

(65) Prior Publication Data

US 2010/0080804 A1    Apr. 1, 2010

Related U.S. Application Data

(60) Continuation of application No. 11/768,156, filed on Jun. 25, 2007, now Pat. No. 7,625,710, which is a continuation of application No. 10/857,664, filed on May 28, 2004, now Pat. No. 7,235,238, which is a continuation of application No. 10/157,447, filed on May 28, 2002, now Pat. No. 7,001,599, which is a continuation of application No. 09/578,178, filed on May 24, 2000, now Pat. No. 6,451,760, which is a division of application No. 09/110,618, filed on Jul. 6, 1998, now Pat. No. 6,090,918, which is a division of application No. 08/604,333, filed on Feb. 21, 1996, now Pat. No. 5,776,731.

(51) Int. Cl.
*A61K 39/00* (2006.01)

(52) U.S. Cl. ............... 424/139.1; 424/141.1; 424/144.1; 530/350

(58) Field of Classification Search ......................... None
See application file for complete search history.

(56) References Cited

U.S. PATENT DOCUMENTS

| 5,488,032 | A  | 1/1996  | Dower et al.  |
| 6,326,472 | B1 | 12/2001 | Timans et al. |
| 6,492,496 | B1 | 12/2002 | Parnet et al. |

OTHER PUBLICATIONS

Arend et al., "Binding of IL-α, I-1L-β, and IL-1 Receptor Antagonist by Soluble IL-1 Receptors and Levels of Soluble IL-1 Receptors in Synovial Fluids," *The Journal of Immunology*, 153(10):4767-4774, Nov. 15, 1994.
Arend, William P., "Interleukin-1 Receptor Antagonist," Advances in Immunology, 54:167-227, Jan. 19, 1993.
Auphan et al., "Immunosuppression by Glucocorticoids: Inhibition of NF-kB Activity Through Induction of IkB Synthesis," *Science*, 270:286-290, Oct. 13, 1995.
Baum et al., "Molecular characterizastion of murine and human OX40/OX40 ligand systems: identification of a human OX40 ligand as the HTLV-1-regulated protein gp34," *The EMBO Journal*, 13(17):3992-4001, 1994.
Bergers et al, "Alternative promoter usage of the Fos-responsive gene Fit-1 generated mRNA isoforms coding for either secreted or membrane-bound proteins related to the IL-1 receptor," *EMBO Journal*, 13(5):1176-1188, 1994.
Buckler et al. "Two-step stimulation of B lymphocytes to enter DNA synthesis: synergy between anti-immunoglobulin antibody and cytochalasin on expression of c-myc and a G1-specific gene," Mol Cell Biol., 8(3):1371-1375 (abstract only), 1988.
Carter et al., "Purification, cloning, expression and biological characterization of an interleukin-1 receptor antagonist protein," Nature, 344:633-637, Apr. 12, 1990.
Crowell et al., "Functional Bowel Disorders and Dysmenorrhea: Don't Cramp My Style," Gastroenterology, 109(3):1017-1019, Sep. 1995.
Dinarello, Charles A., "Interleukin-1 and Its Biologically Related Cytokines," Advances in Immunology, 44:153-205, 1989.
Fauci, Anthony S., :Multifactorial Nature of Human Immunodeficiency Virus Disease: Implications for Therapy, Science, 262:1011-1014, Nov. 12, 1993.
Greenfeder et al., "Molecular Cloning and Characterization of a Second Subunit of the Interleukin I Receptor Complex," The Journal of Biological Chemistry, 270(23):13757-13765, 1995.
Hashimoto et al., "The *Toll* Gene of *Drosophila*, Required for Dorsal-Ventral Embryonic Polarity, Appears to Encode a Transmembrane Protein," *Cell*, 52:269-27, Jan. 29, 1988.
Howard et al., "Soluble tumor necrosis factor receptor: Inhibition of human immunodeficiency virus activation," *Proc. Natl. Acad. Sci. USA*, p. 2335, Mar. 1993.
Isselbacher et al., "Eicosanoids and Human Disease," *Harrison's Principles of Internal Medicine*, 1(13):433-435, 13th Ed. 1994.
Lord et al., "Nucleotide sequence and expression of a cDNA encoding MyD88, a novel myeloid differentiation primary response gene induced by IL6," Oncogene, 5(7):1095-1097, Jul. 1990.
Marx, Jean, "How the Glucocorticoids Suppress Immunity," *Science*, 270:232-233, Oct. 13, 1995.
Nomura et al., Prediction of the Coding Sequences of Unidentified Human Genes. I. The Coding Sequences of 40 New Genes (KIAA0001-KIAA0040) Deduced by Analysis of Randomly Sampled cDNA Clones from Human Immature Myeloid Cell Line KG-1, DNA Research, 1:27-35, 1994.
Parnet et al., "IL-1Rrp is a novel receptor-like molecule similar to the type I interleukin-1 receptor and its homologues T1/ST2 and IL-1R AcP," J Biol Chem 271(8):3967-3970, 1996.
Parnet et al., "A Novel Receptor Similar to the Type I Interleukin I Receptor and T1/ST2," Poster presented at Lake George, NY, Oct. 1995.
Price et al., "Pathophysiology Clinical Concepts of Disease Processes," p. 36-38, 1986.
Reznikov et al., "IL-18 binding protein increases spontaneous and IL-1-induced prostaglandin production via inhibition of IFN-gamma," Proc Natl Acad Sci USA 97(5):2174-2179, 2000.

(Continued)

*Primary Examiner* — Dong Jiang
(74) *Attorney, Agent, or Firm* — Thomas J. Wrona

(57) ABSTRACT

2F1 polypeptides are provided, along with DNA sequences, expression vectors and transformed host cells useful in producing the polypeptides. Soluble 2F1 polypeptides find use in inhibiting prostaglandin synthesis and treating inflammation.

24 Claims, No Drawings

OTHER PUBLICATIONS

Rosenberg et al., Immunopathogenesis of HIV Infection, FASEB Journal. 5: p. 2384, Jul. 1991.

Sha et al., "Targeted Disruption of the p50 Subunit of NF-kB Leads to Multifocal Defects in Immune Responses," *Cell*, 80:321-330, Jan. 27, 1995.

Sims et al., "Geonomic Organization of the Type I and Type II IL-1 Receptors," Cytokine, 7(6):483-490, Aug. 1995.

Thanos et al., NF-kB: A Lesson in Family Values, Cell, 80:529-532, Feb. 24, 1995.

Tietz, Norbert W., "7-Lipids, Lipoproteins, and Apolipoproteins," *Textbook of Clinical Chemistry* p. 842, 1986.

Torigoe et al., "Purification and characterization of the human interleukin-18 receptor," J. Biol. Chem. And Mole. Biol., 272(41):25737-24742, 1997.

Weih et al., "Multiorgan Inflammation and Hematopoietic Abnormalities in Mice with a Targeted Disruption of ReIB, a Member of the NF-kB/Rel Family," *Cell*, 80:331-340, Jan. 27, 1995.

Yamamoto et al., "Transcriptional Roles of Nuclear Factor kB and Nuclear Factor-Interleukin-6 in the Tumor Necrosis Factor α-Dependent Induction of Cyclooxygenase-2 in MC3T3-E1 Cells," *The Journal of Biological Chemistry*, 270(52):31315-31320, 1995.

METHODS OF TREATING INFLAMMATORY DISORDERS OF THE LUNGS

CROSS-REFERENCE TO RELATED APPLICATIONS

This application is a Continuation of U.S. patent application Ser. No. 11/768,156, filed Jun. 25, 2007, now issued as U.S. Pat. No. 7,625,710, which is a Continuation of U.S. patent application Ser. No. 10/857,664, filed May 28, 2004, now issued as U.S. Pat. No. 7,235,238, which is a Continuation of U.S. patent application Ser. No. 10/157,447, filed May 28, 2002, now issued as U.S. Pat. No. 7,001,599, which is a Continuation of U.S. patent application Ser. No. 09/578,178, filed May 24, 2000, now issued as U.S. Pat. No. 6,451,760, which is a Divisional of U.S. patent application Ser. No. 09/110,618, filed Jul. 6, 1998, now issued as U.S. Pat. No. 6,090,918, which is a Divisional of U.S. patent application Ser. No. 08/604,333, filed Feb. 21, 1996, now issued as U.S. Pat. No. 5,776,731, which are hereby incorporated by reference.

REFERENCE TO THE SEQUENCE LISTING

The present application is being filed along with a Sequence Listing in electronic format. The Sequence Listing is provided as a file entitled 2619USCNT4_REV_SEQUENCE_LISTING.txt, created Nov. 20, 2009, which is 27 KB in size. The information in the electronic format of the Sequence Listing is incorporated herein by reference in its entirety.

BACKGROUND OF THE INVENTION

The type I interleukin-1 receptor (IL-1RI) mediates the biological effects of interleukin-1, a pro-inflammatory cytokine (Sims et al., *Science* 241:585-589, 1988; Curtis et al., *Proc. Natl. Acad. Sci. USA* 86:3045-3049, 1989). A second interleukin-1 receptor (designated type II IL-1R or IL-1RII) binds IL-1, but does not appear to mediate signal transduction (McMahan et al., *EMBO J.* 10:2821, 1991; Sims et al., *Proc. Natl. Acad. Sci. USA* 90:6155-6159, 1993). IL-1RI and IL-1RII each bind IL-1α and IL-1β.

IL-1RI and IL-1RII belong to a family of proteins that exhibit significant sequence homology. One such protein is IL-1R accessory protein (IL-1R AcP), described in Greenfeder et al. (*J. Biol. Chem.* 270: 13757-13765, 1995). This protein, by itself, is not capable of binding IL-1, but does form a complex with IL-1RI and either IL-1α and IL-1β. When co-expressed with IL-1RI, recombinant IL-1R AcP increases the binding affinity of IL-1RI for IL-1β (Greenfeder et al., supra).

The protein variously known as ST2, ST2L, T1, or Fit-1 also is a member of the IL-1R family, but does not bind IL-1. Cloning of mouse and rat cDNAs encoding membrane-bound and secreted forms of this protein has been reported (Klemenz et al., *Proc. Natl. Acad. Sci. USA* 86:5708, 1989; Tominaga, *FEBS LETTERS* 258:301, 1989; Yanagisawa et al., *FEBS LETTERS* 318:83, 1993; Bergers et al., *EMBO J.* 13:1176, 1994). Human ST2 cDNA and genomic clones have been isolated as well (Tominaga et al. *Biochimica et Biophysica Acta* 1171:215, 1992).

Other proteins exhibiting significant sequence homology with IL-1RI are murine MyD88 (Lord et al., *Oncogene* 5: 1095-1097, 1990), human rsc786 (Nomura et al., *DNA Res.* 1:27-35, 1994), and a number of *Drosophila* proteins, the best characterized of which is Toll (Hashimoto et al., *Cell* 52, 269-279, 1988). The tobacco N gene (Whitham et al., *Cell* 78:1101-1115, 1994) is among the additional IL-1R family members.

MyD88, rsc786, Toll, and the tobacco N gene product contain domains exhibiting significant homology to the cytoplasmic domain of the IL-1RI. The IL-1R AcP and ST2 proteins exhibit sequence similarity to IL-1RI in both their extracellular and cytoplasmic portions. The B16R protein of vaccinia virus (Goebel et al., *Virology* 179:247, 1990) appears to be a viral homolog of IL-1RII.

Identification of additional receptors of this family is desirable. Such receptor proteins can be studied to determine whether or not they bind IL-1, and, if so, whether the receptors play a role in mediating signal transduction. The possible existence of additional affinity-converting subunits for receptors of this family can be explored, as well.

SUMMARY OF THE INVENTION

The present invention provides a novel receptor protein designated 2F1. Both soluble and membrane-bound forms of 2F1 are disclosed herein. The present invention also provides isolated DNA encoding 2F1 proteins, expression vectors comprising the isolated DNA, and a method for producing 2F1 by cultivating host cells transformed with the expression vectors under conditions appropriate for expression of the 2F1 protein. Antibodies directed against 2F1 are also disclosed. 2F1 finds use in inhibiting prostaglandin synthesis and alleviating inflammation.

DETAILED DESCRIPTION OF THE INVENTION

DNA encoding a novel receptor protein designated 2F1 has been isolated in accordance with the present invention. Expression vectors comprising the 2F1 DNA are provided, as well as methods for producing recombinant 2F1 polypeptides by culuring host cells containing the expression vectors under conditions appropriate for expression of 2F1, then recovering the expressed 2F1 protein. Purified 2F1 protein is also encompassed by the present invention, including soluble forms of the protein comprising the extracellular domain.

The present invention also provides 2F1 and immunogenic fragments thereof that may be employed as immunogens to generate antibodies specific thereto. In one embodiment, the antibodies are monoclonal antibodies.

Human 2F1 clones were isolated as described in example 1. A human 2F1 DNA sequence is presented in SEQ ID NO:1, and the amino acid sequence encoded thereby is presented in SEQ ID NO:2. The protein includes a signal peptide (amino acids −19 to −1) followed by an extracellular domain (amino acids 1 to 310), a transmembrane region (amino acids 311 to 332), and a cytoplasmic domain (amino acids 333 to 522).

Mouse 2F1 cDNA was isolated by cross-species hybridization, as described in example 2. The DNA and encoded amino acid sequences of this mouse 2F1 DNA are presented in SEQ ID NO:3 and SEQ ID NO:4. The protein of SEQ ID NO:4 comprises a signal peptide (amino acids −18 to −1), an extracellular domain (amino acids 1 to 307), a transmembrane region (amino acids 308 to 330), and a cytoplasmic domain (amino acids 331 to 519). The mouse and human 2F1 amino acid sequences are 65% identical.

The amino acid sequence of the 2F1 protein indicates that it is a member of the IL-1 receptor family. Of the known IL-1 receptor family members, 2F1 has the highest degree of sequence homology with IL-1R accessory protein (IL-1R AcP), T1/ST2, and type I IL-1 receptor (IL-1RI). The murine 2F1 amino acid sequence of SEQ ID NO:4 is 31% identical to the amino acid sequence of murine IL-1R AcP, 30% identical to that of the full length murine T1/ST2, and 27% identical to that of the murine IL-1RI. The cytoplasmic domains show slightly greater sequence conservation (36%-44%) than do the extracellular portions (20%-27%).

The binding assay described in example 3 was conducted to determine whether 2F1 binds IL-1α, IL-1β, or 1L-1 receptor antagonist. Although 2F1 is a member of the IL-1 receptor family, it did not bind any of the three proteins tested.

Human and mouse 2F1 are within the scope of the present invention, as are 2F1 proteins derived from other organisms, including but not limited to mammalian species such as rat, bovine, porcine, or various non-human primates. DNA encoding 2F1 proteins from additional organisms can be identified by cross-species hybridization techniques. Messenger RNAs isolated from various cell types can be screened in Northern blots to determine a suitable source of mRNA for use in cloning 2F1 cDNA from other species.

The term "2F1" as used herein refers to a genus of polypeptides that are substantially homologous to a native 2F1 protein (e.g., the protein of SEQ ID NO:2 or 4), and which exhibit a biological activity of a native 2F1 protein. 2F1 proteins of the present invention include membrane-bound proteins (comprising an extracellular domain, a transmembrane region, and a cytoplasmic domain) as well as truncated proteins that retain a desired property. Such truncated proteins include, for example, soluble 2F1 comprising only the extracellular domain or a fragment thereof. Also included are variants of native 2F1 proteins, wherein the variants retain a desired biological activity of a native 2F1. Such variants are described in more detail below.

A 2F1 polypeptide, or fragment or variant thereof, can be tested for biological activity in any suitable assay. When the cytoplasmic domain is altered (e.g., truncated, or altered by deletion, addition, or substitution of amino acid residues), the 2F1 polypeptide can be tested for biological activity in a signal transduction assay. Such assays include, but are not limited to, those described in examples 5 to 7 below. The altered cytoplasmic domain can be fused to the extracellular domain of an IL-1 receptor, and the resulting chimeric receptor tested for the ability to respond to IL-1 by NF-κB activation (see the procedure in example 5), induction of IL-8 promoter function (example 6), or stimulation of prostaglandin $E_2$ synthesis (example 7). 2F1 polypeptides that include an extracellular domain (e.g., soluble 2F1, as described below) can be tested for the ability to inhibit prostaglandin $E_2$ synthesis in vivo in animal studies. The 2F1 is administered in vivo, and prostaglandin $E_2$ levels in the animals are measured (before and after administration of 2F1, and compared to control animals) by any suitable means, e.g., by ELISA.

One embodiment of the present invention is directed to soluble 2F1 polypeptides. Soluble 2F1 polypeptides comprise all or part of the extracellular domain of a native 2F1, but lack the transmembrane region that would cause retention of the polypeptide on a cell membrane. When initially synthesized, soluble 2F1 polypeptides advantageously comprise the native (or a heterologous) signal peptide to promote secretion, but the signal peptide is cleaved upon secretion of 2F1 from the cell.

One use of soluble 2F1 polypeptides is in blocking a biological activity of 2F1. Soluble 2F1 may be administered to a mammal to bind any endogenous 2F1 ligand(s), thereby inhibiting the binding of such ligands to endogenous receptors comprising 2F1. In one embodiment, a soluble 2F1 polypeptide is administered to treat pain or inflammation by inhibiting prostaglandin synthesis, as discussed in more detail below.

Soluble 2F1 may be identified (and distinguished from its non-soluble membrane-bound counterparts) by separating intact cells which express the desired protein from the culture medium, e.g., by centrifugation, and assaying the medium (supernatant) for the presence of the desired protein. The presence of 2F1 in the medium indicates that the protein was secreted from the cells and thus is a soluble form of the desired protein. Soluble 2F1 may be a naturally-occurring form of this protein.

The use of soluble forms of 2F1 is advantageous for certain applications. Purification of the proteins from recombinant host cells is facilitated, since the soluble proteins are secreted from the cells. Further, soluble proteins are generally more suitable for intravenous administration.

Examples of soluble 2F1 polypeptides include those comprising the entire extracellular domain of a native 2F1 protein. One such polypeptide is a soluble human 2F1 comprising amino acids 1 through 310 of SEQ ID NO:2. Another is a soluble murine 2F1 comprising amino acids 1 through 307 of SEQ ID NO:4. When initially expressed within a host cell, the soluble polypeptide may additionally comprise one of the heterologous signal peptides described below that is functional within the host cells employed. Alternatively, the polypeptide may comprise the native signal peptide, such that the 2F1 comprises amino acids −19 through 310 of SEQ ID NO:2 or amino acids −18 through 307 of SEQ ID NO:4. Soluble 2F1 polypeptides include fragments of the extracellular domain that retain a desired biological activity. DNA sequences encoding soluble 2F1 polypeptides are encompassed by the present invention.

2F1 fragments, including soluble polypeptides, may be prepared by any of a number of conventional techniques. A desired DNA sequence may be chemically synthesized using known techniques. DNA fragments also may be produced by restriction endonuclease digestion of a full length cloned DNA sequence, and isolated by electrophoresis on agarose gels. Oligonucleotides that reconstruct the 5' or 3' end of a DNA fragment to a desired point may be synthesized. The oligonucleotides may contain a restriction endonuclease cleavage site upstream of the desired coding sequence and position an initiation codon (ATG) at the 5' terminus of the coding sequence. Linkers containing restriction endonuclease cleavage site(s) may be employed to insert the desired DNA fragment into an expression vector. Alternatively, known mutagenesis techniques may be employed to insert a stop codon at a desired point, e.g., immediately downstream of the codon for the last amino acid of the extracellular domain.

As a further alternative, the well known polymerase chain reaction (PCR) procedure may be employed to isolate a DNA sequence encoding a desired protein fragment. Oligonucleotides that define the termini of the desired fragment are employed as primers in the reaction. PCR procedures are described, for example, in Saiki et al. (*Science* 239:487, 1988) and in *Recombinant DNA Methodology*, Wu et al. eds., Academic Press Inc., San Diego, 1989, pp 189-196.

Regarding the foregoing discussion of signal peptides and the various domains of the 2F1 proteins, the skilled artisan will recognize that the above-described boundaries of such regions of the proteins are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, the exact boundaries of a transmembrane region may differ from that predicted by a computer program. Such forms of 2F1 that retain a desired biological activity are included among the 2F1 polypeptides of the present invention.

The present invention provides purified 2F1 polypeptides, both recombinant and non-recombinant. Variants and derivatives of native 2F1 proteins that retain a desired biological activity are also within the scope of the present invention. 2F1 variants may be obtained by mutations of nucleotide sequences coding for native 2F1 polypeptides. A 2F1 variant, as referred to herein, is a polypeptide substantially homologous to a native 2F1, but which has an amino acid sequence different from that of a native 2F1 because of one or more deletions, insertions or substitutions.

The variant amino acid sequence preferably is at least 80% identical to a native 2F1 amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

DNA encoding such variants is provided by the present invention as well. Such DNA sequences preferably are at least 80% identical to a native 2F1 DNA sequence, most preferably at least 90% identical. The percent identity may be determined using known computer programs, such as the above-described GAP program.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Variants include conservatively substituted sequences, meaning that one or more amino acid residues of a native 2F1 is replaced by a different residue, but that the conservatively substituted 2F1 polypeptide retains a desired biological activity of the native protein. Examples of conservative substitutions include substitution of residues that do not alter the secondary or tertiary structure of the protein.

A given amino acid may be replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other conservative substitutions, e.g., involving substitutions of entire regions having similar hydrophobicity characteristics, are well known.

2F1 proteins also may be modified to create 2F1 derivatives by forming covalent or aggregative conjugates with other chemical moieties, such as glycosyl groups, lipids, phosphate, acetyl groups and the like. Covalent derivatives of 2F1s may be prepared by linking the chemical moieties to functional groups on 2F1 amino acid side chains, or at the N-terminus or C-terminus of an 2F1 polypeptide or the extracellular domain thereof. Other derivatives of 2F1 within the scope of this invention include covalent or aggregative conjugates of 2F1s with other proteins or polypeptides, e.g., N-terminal or C-terminal fusions produced by recombinant DNA technology. For example, the conjugate may comprise a heterologous signal or leader polypeptide sequence at the N-terminus of a 2F1 polypeptide. The signal or leader peptide co-translationally or post-translationally directs transfer of the conjugate from its site of synthesis to a site inside or outside of the cell membrane or cell wall.

2F1 polypeptide fusions can comprise peptides added to facilitate purification and identification of 2F1. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:5), which is highly antigenic and provides an epitope reversibly bound by a specific monoclonal antibody, enabling rapid assay and facile purification of expressed recombinant protein. Expression systems useful for fusing the Flag® octapeptide to the N- or C-terminus of a given protein are available from Eastman Kodak Co., Scientific Imaging Systems Division, New Haven, Conn., as are monoclonal antibodies that bind the octapeptide.

The present invention further includes 2F1 polypeptides with or without associated native-pattern glycosylation. 2F1 expressed in yeast or mammalian expression systems may be similar to or significantly different from a native 2F1 polypeptide in molecular weight and glycosylation pattern, depending upon the choice of expression system. Expression of 2F1 polypeptides in bacterial expression systems, such as *E. coli*, provides non-glycosylated molecules.

N-glycosylation sites in the 2F1 extracellular domain can be modified to preclude glycosylation. N-glycosylation sites in eukaryotic polypeptides are characterized by an amino acid triplet Asn-X-Y, wherein X is any amino acid except Pro and Y is Ser or Thr. The human 2F1 protein extracellular domain contains such triplets at amino acids 72-74, 83-85, 131-133, 149-151, 178-180, 184-186, 217-219, and 278-280 of SEQ ID NO:2. The murine 2F1 protein contains such triplets at amino acids 32-34, 53-55, 89-91, 93-95, 116-118, 171-173, 176-178, 182-184, 215-217, 277-279, and 460-462 of SEQ ID NO:4. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

Additional variants are those in which cysteine residues that are not essential for biological activity are deleted or replaced with other amino acids, preventing formation of incorrect intramolecular disulfide bridges upon renaturation. As with the other IL-1R family members, the extracellular domain of 2F1 contains three immunoglobulin-like (Ig) domains. Based on alignment of the human 2F1 amino acid sequence with that of other family members, the cysteines predicted to form the typical intradomain disulfide bonds of the Ig domains are located at positions 121, 166, 218, and 279 of SEQ ID NO:2. The first (most N-terminal) Ig domain includes the first (residue 22) but lacks the second cysteine of the pair conserved in other proteins of this family. The first Ig domain of 2F1 thus is predicted to lack the intradomain disulfide bond that is typical of Ig domains. Like all IL-1R-like proteins except T1/ST2, mouse and human 2F1 also have a cysteine residue just a few residues C-terminal to the point of signal peptide cleavage (the cysteine at position 2 of SEQ ID NO:2 and at position 4 of SEQ ID NO:4). 2F1 fragments and variants preferably contain these conserved cysteines.

Other variants are prepared by modification of adjacent dibasic amino acid residues to enhance expression in yeast systems in which KEX2 protease activity is present. EP 212, 914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Human 2F1 contains such KEX2 protease processing sites at amino acids 94-95, 296-297, 345-346, 418-419, and 448-449 of SEQ ID NO:2. Murine 2F1 contains KEX2 protease processing sites at amino acids 87-88, 96-97, 231-232, 244-245, 295-296, 339-340, 416-417, 432-433, and 446-447 of SEQ ID NO:4. Lys-Lys pairings are considerably less susceptible to KEX2 cleavage, and conversion of Arg-Lys or Lys-Arg to Lys-Lys represents a conservative and preferred approach to inactivating KEX2 sites.

Naturally occurring 2F1 variants are also encompassed by the present invention. Examples of such variants are proteins that result from alternative mRNA splicing events or from proteolytic cleavage of the 2F1 protein, wherein a desired biological activity is retained. Alternative splicing of mRNA may yield a truncated but biologically active 2F1 protein, such as a naturally occurring soluble form of the protein, for example. Variations attributable to post-translational processing or proteolysis include, for example, differences in the N- or C-termini upon expression in different types of host cells, due to proteolytic removal of one or more terminal amino acids from the 2F1 protein (generally from 1-5 terminal amino acids).

2F1 proteins in which differences from the amino acid sequence of SEQ ID NO:2 are attributable to genetic polymorphism (allelic variation among individuals producing the protein) are also among the naturally occurring variants contemplated herein. The human 2F1 sequence presented in SEQ ID NO:1 is derived from three cDNA clones from a peripheral blood lymphocyte library and four PCR clones from the epidermal carcinoma line KB (see example 1). The codon for alanine 298 is polymorphic, being present in the PBL clones and two of the KB clones, and absent from the other two KB clones. It is also absent from the two mouse clones that were derived from an EL4 T cell library. The present invention thus provides human 2F1 proteins either containing or lacking an alanine residue at position 298.

The present invention provides isolated DNA sequences encoding the novel 2F1 polypeptides disclosed herein. 2F1-encoding DNA encompassed by the present invention includes, for example, cDNA, chemically synthesized DNA, DNA isolated by PCR, genomic DNA, and combinations thereof. Genomic 2F1 DNA may be isolated by conventional techniques, e.g., by using the DNA of SEQ ID NOS:1 or 3, or a fragment thereof, as a probe in a hybridization procedure.

Particular embodiments of the present invention are directed to an isolated DNA comprising nucleotides 1 to 1626 of SEQ ID NO:1 (the entire coding region), nucleotides 58 to 1626 of SEQ ID NO:1 (encoding mature human 2F1), nucleotides 381 to 1994 of SEQ ID NO:3 (the entire coding region), or nucleotides 435 to 1994 of SEQ ID NO:3 (encoding mature murine 2F1). In other embodiments, isolated DNA sequences encode a 2F1 fragment, such as one of the above-described soluble polypeptides. Such DNAs include a DNA comprising nucleotides 1 to 985 of SEQ ID NO:1 (which encode amino acids −19 to 310 of SEQ ID NO:2), nucleotides 58 to 985 of SEQ ID NO:1 (which encode amino acids 1 to 310 of SEQ ID NO:2), nucleotides 381 to 1355 of SEQ ID NO:3 (which encode amino acids −18 to 307 of SEQ ID NO:4), and nucleotides 435 to 1355 of SEQ ID NO:3 (which encode amino acids 1 to 307 of SEQ ID NO:4). DNAs encoding the various forms of 2F1 disclosed herein, e.g., 2F1 variants and fusion proteins, are encompassed by the present invention.

Nucleic acid sequences within the scope of the present invention include isolated DNA and RNA sequences that hybridize to the native 2F1 nucleotide sequences disclosed herein under moderately or highly stringent conditions, and which encode biologically active 2F1. Moderate stringency hybridization conditions refer to conditions described in, for example, Sambrook et al., *Molecular Cloning: A Laboratory Manual,* 2 ed. Vol. 1, pp. 1.101-104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0), hybridization at about 55° C. in 5×SSC overnight, followed by washing at 50-55° C. in 2×SSC, 0.1% SDS. Highly stringent conditions include higher temperatures of hybridization and washing. The skilled artisan will recognize that the temperature and wash solution salt concentration may be adjusted as necessary according to factors such as the length of the probe. In one embodiment, highly stringent conditions include hybridization at 68° C. followed by washing in 0.1× SSC/0.1% SDS at 68° C.

Due to the known degeneracy of the genetic code, wherein more than one codon can encode the same amino acid, a DNA sequence may vary from that presented in SEQ ID NO:1 or 3, and still encode an 2F1 protein having the amino acid sequence of SEQ ID NO:2 or 4, respectively. Such variant DNA sequences may result from silent mutations that occur during PCR amplification, for example. Alternatively, the variant sequence may be the product of deliberate mutagenesis of a native sequence.

The present invention thus provides isolated DNA sequences encoding biologically active 2F1, selected from: (a) DNA derived from the coding region of a native mammalian 2F1 gene (e.g., DNA comprising the coding region of the nucleotide sequence presented in SEQ ID NO:1 or 3); (b) DNA capable of hybridization to a DNA of (a) under moderately or highly stringent conditions; and (c) DNA which is degenerate as a result of the genetic code to a DNA defined in (a) or (b). The 2F1 proteins encoded by such DNA sequences are encompassed by the present invention.

Examples of 2F1 proteins encoded by DNA that varies from the native DNA sequence of SEQ ID NO:1 or 3, wherein the variant DNA will hybridize to the native DNA sequence under moderately or highly stringent conditions, include, but are not limited to, 2F1 fragments and 2F1 proteins comprising inactivated N-glycosylation site(s) or inactivated KEX2 protease processing site(s). Further examples are 2F1 proteins encoded by DNA derived from other mammalian species, wherein the DNA will hybridize to the human DNA of SEQ ID NO:1 or the mouse DNA of SEQ ID NO:3.

Purified 2F1 Protein and Uses Thereof

The present invention provides purified 2F1 polypeptides, which may be produced by recombinant expression systems as described below or purified from naturally occurring cells. Conventional protein purification techniques may be employed.

The desired degree of purity may depend on the intended use of the protein. A relatively high degree of purity is desired when the protein is to be administered in vivo, for example. Advantageously, 2F1 polypeptides are purified such that no protein bands corresponding to other (non-2F1) proteins are detected by SDS-polyacrylamide gel electrophoresis (SDS-PAGE). It will be recognized by one skilled in the pertinent field that multiple bands corresponding to 2F1 protein may be detected by SDS-PAGE, due to differential glycosylation, variations in post-translational processing, and the like, as discussed above. Most preferably, 2F1 is purified to substantial homogeneity, as indicated by a single protein band upon analysis by SDS-PAGE. The protein band may be visualized by silver staining, Coomassie blue staining, or (if the protein is radiolabeled) by autoradiography.

One process for producing the 2F1 protein comprises culturing a host cell transformed with an expression vector comprising a DNA sequence that encodes 2F1 under conditions such that 2F1 is expressed. The 2F1 protein is then recovered from culture medium or cell extracts, depending upon the expression system employed. As the skilled artisan will recognize, procedures for purifying the recombinant 2F1 will vary according to such factors as the type of host cells employed and whether or not the 2F1 is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify 2F1. Some or all of the foregoing purification steps, in various combinations, can be employed to provide a substantially homogeneous recombinant protein.

It is also possible to utilize an affinity column comprising an antibody that binds 2F1 to purify 2F1 polypeptides by immunoaffinity chromatography. Example 8 describes a procedure for employing the 2F1 protein of the present invention as an immunogen to generate monoclonal antibodies.

The foregoing chromatography procedures are among those that may be employed to purify either recombinant or non-recombinant 2F1. Recombinant cell culture enables the production of the protein free of those contaminating proteins that may be normally associated with 2F1 as it is found in nature, e.g., on the surface of certain cell types.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

2F1 preferably is expressed as a secreted polypeptide to simplify purification. Secreted recombinant polypeptides from a yeast host cell fermentation can be purified by methods analogous to that disclosed by Urdal et al. (*J. Chromatog.* 296:171, 1984), which includes two sequential, reversed-phase HPLC steps.

Conjugates comprising a 2F1 polypeptide and a detectable agent are provided herein. The agent preferably is covalently bound to the 2F1 polypeptide. Such conjugates find use in in vitro assays, for example.

Suitable agents include, but are not limited to, radionuclides, chromophores, fluorescent compounds, enzymes that catalyze a colorimetric or fluorometric reaction, and the like, with the particular agent being chosen according to the intended application. Suitable radionuclides include, but are not limited to, $^{123}$I, $^{131}$I, $^{99m}$Tc, $^{111}$In, and $^{76}$Br.

The agents may be attached to the 2F1 using any of the conventional methods by which such compounds are attached to polypeptides in general. Functional groups on amino acid side chains of an 2F1 may be reacted with functional groups on a desired agent to form covalent bonds, for example. The agent may be covalently linked to 2F1 via an amide bond, hindered disulfide bond, acid-cleavable linkage, and the like, which are among the linkages that may be chosen according to such factors as the structure of the desired agent. Alternatively, the 2F1 or the agent may be derivatized to generate or attach a desired reactive functional group. The derivatization may involve attachment of one of the bifunctional coupling reagents available for linking various molecules to proteins (Pierce Chemical Company, Rockford Ill.). A number of techniques for radiolabeling proteins are known. Radionuclide metals may be attached to 2F1 using a suitable bifunctional chelating agent, examples of which are described in U.S. Pat. Nos. 4,897,255 and 4,965,392.

As described in example 7, the signaling (cytoplasmic) domain of 2F1 transduces a biological signal that stimulates prostaglandin $E_2$ synthesis. Prostaglandins are naturally occurring long-chain hydroxy fatty acids exhibiting biological effects that include, inter alia, mediating pain and inflammation.

One embodiment of the present invention is directed to the use of soluble 2F1 polypeptides to inhibit prostaglandin synthesis. In vivo, signal transduction may be initiated by the binding of unidentified ligand(s) to receptors comprising 2F1. Soluble 2F1 is administered to a mammal to bind such ligands, thereby inhibiting ligand binding to endogenous cell surface 2F1.

Soluble 2F1 polypeptides may be administered to a mammal to treat conditions that are mediated by a prostaglandin. A condition is said herein to be mediated by a prostaglandin when the condition is, at least in part, caused or exacerbated (directly or indirectly) by a prostaglandin.

Such conditions include, but are not limited to, inflammation associated with arthritis (especially rheumatoid arthritis and osteoarthritis), inflammation of the lungs associated with allergy or asthma, adult respiratory distress syndrome, inflammatory bowel disease, and inflammation resulting from injury (especially injury of a joint). The desirability of inhibiting prostaglandins to treat fever, Bartter's syndrome, diabetes mellitus, patent ductus arteriosus, and dysmenorrhea is discussed in *Harrisons's Principles of Internal Medicine*, 13th Edition, Vol. 1, Isselbacher et al., Eds., McGraw-Hill, Inc. New York, 1994, pp 433-435.

Prostaglandin $E_2$ ($PGE_2$) also has been implicated in bone resorption, including the bone resorption associated with rheumatoid arthritis and periodontal disease (Isselbacher et al., Eds., supra, at page 434). $PGE_2$ has been reported to cause increased vascular permeability, which is an aspect of the inflammatory response that can lead to local edema (Isselbacher et al., Eds., supra, at page 435). Prostaglandins and their role in inflammation are discussed further in *Pathophysiology: Clinical Concepts of Disease Processes*, 3rd Edition, Price and Wilson, Eds., McGraw-Hill Book Company, New York, 1986, pp 36-38; and *Inflammation: Basic Principles and Clinical Correlates*, Second Edition, Galin et al., Eds., Raven Press, New York, 1992.

Prostaglandins have been suggested to play roles in modulating the immune response. $PGE_2$ can suppress mitogen-induced stimulation of human lymphocytes, for example. Inhibition of $PGE_2$ thus may be beneficial in patients in which depressed cellular immunity is attributable, at least in part, to the action of prostaglandins. (See Isselbacher et al., Eds., supra, at page 435). Roles for $PGE_1$ and $PGE_2$ in angiogenesis have also been suggested.

It is notable that the 2F1 signaling domain transduced a signal that resulted in activation of the transcription factor NF-κB (see example 5). The anti-inflammatory effect of certain drugs (glucocorticoids) is believed to be attributable, at least in part, to inhibition of NF-κB activation (Auphan et al., *Science* 270:286-290, 1995; Marx, *Science* 270:232-233, 1995). Soluble 2F1 polypeptides thus may be used to inhibit NF-κB activation signals transduced via 2F1.

NF-κB activation has been linked to TNF-induced replication of human immunodeficiency virus (HIV) in infected cells, including T cells (Howard et al., *Proc. Natl. Acad. Sci. USA* 90:2335-2339, 1993). 2F1 is expressed on T-cells, and an NF-κB activation signal is transduced by the 2F1 signaling domain. Thus, soluble 2F1 may be employed to reduce HIV expression in HIV-infected cells. An effective amount of soluble 2F1 is administered in vivo to inhibit NF-κB activation that results from signaling through 2F1. Any HIV replication that would have resulted from such NF-κB activation is thus diminished.

Oligomeric Forms of 2F1

Encompassed by the present invention are oligomers, such as dimers, trimers, or higher oligomers, that contain 2F1. Such oligomers may be naturally occurring or produced by means such as recombinant DNA technology.

The 2F1 moieties of the oligomer may be soluble 2F1 polypeptides. In certain embodiments, the oligomers comprise from two to four 2F1 polypeptides.

Oligomers may be formed by disulfide bonds between cysteine residues on different 2F1 polypeptides, or by non-covalent interactions between 2F1 polypeptide chains, for example. In other embodiments, oligomers comprise multiple 2F1 polypeptides joined via covalent or non-covalent interactions between peptide moieties fused to the 2F1 polypeptides. Such peptides may be peptide linkers (spacers), or peptides that have the property of promoting oligomerization. Leucine zippers and certain polypeptides derived from antibodies are among the peptides that can promote oligomerization of 2F1 polypeptides attached thereto, as described in more detail below.

Preparation of fusion proteins comprising heterologous polypeptides fused to various portions of antibody-derived polypeptides (including the Fc domain) has been described, e.g., by Ashkenazi et al., (*PNAS USA* 88:10535, 1991); Byrn et al., (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992). In one embodiment of the invention, a 2F1 dimer is created by fusing a 2F1 to the Fc region of an antibody (IgG1). The Fc polypeptide preferably is fused to the C-terminus of a soluble 2F1. A gene fusion encoding the 2F1/Fc fusion protein is inserted into an appropriate expression vector. The 2F1/Fc fusion proteins are expressed in host cells transformed with the recombinant expression vector and allowed to assemble much like antibody molecules, whereupon interchain disulfide bonds form between Fc polypeptides to yield divalent 2F1. The desired dimer may be recovered by conventional procedures, e.g., by affinity chromatography employing a protein A or protein G column that will bind the Fc moieties.

The term "Fc polypeptide" as used herein includes native and mutein forms of polypeptides derived from the Fc region of an antibody. Truncated forms of such polypeptides containing the hinge region that promotes dimerization are also included. One suitable Fc polypeptide is described in PCT application WO 93/10151, hereby incorporated by reference. This Fc polypeptide is a single chain polypeptide extending from the N-terminal hinge region to the native C-terminus (i.e., is an essentially full length antibody Fc region). Another useful Fc polypeptide is described in U.S. Pat. No. 5,457,035. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for Fc receptors. Procedures for preparing a fusion protein containing an Fc or Fc mutein polypeptide are described further in Baum et al. (*EMBO J.* 13:3992-4001, 1994).

In other embodiments, 2F1 may be substituted for the variable portion of an antibody heavy or light chain. If fusion proteins are made with both heavy and light chains of an antibody, it is possible to form an 2F1 oligomer with as many as four 2F1 extracellular regions.

Another method for preparing oligomeric 2F1 involves use of a leucine zipper. Leucine zipper domains are peptides that promote oligomerization of the proteins in which they are found. Originally identified in several DNA-binding proteins (Landschulz et al., *Science* 240:1759, 1988), leucine zippers have since been found in a variety of different proteins. Among the known leucine zippers are naturally occurring peptides and derivatives thereof that dimerize or trimerize. Examples of leucine zipper domains suitable for producing soluble oligomeric proteins are those described in PCT application WO 94/10308. Peptides that preferentially form trimers include, for example, the leucine zipper derived from lung surfactant protein D (SPD) described in Hoppe et al. (*FEBS Letters* 344:191, 1994), and U.S. patent application Ser. No. 08/446,922, hereby incorporated by reference. Recombinant fusion proteins comprising a soluble 2F1 polypeptide fused to a leucine zipper peptide are expressed in suitable host cells, and the resulting soluble oligomeric 2F1 that forms is recovered from the culture supernatant.

As a further alternative, oligomeric 2F1 may be expressed as a recombinant fusion protein, with or without peptide linkers between the 2F1 moieties. Suitable peptide linkers are known in the art, and may be employed according to conventional techniques. Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences encoding 2F1, using any suitable conventional technique. In one embodiment, two soluble 2F1 polypeptides are joined by a peptide linker.

The above-described oligomers may be purified by conventional protein purification procedures. Immunoaffinity chromatography using an antibody directed against 2F1 may be employed, for example. Oligomers containing antibody-derived Fc polypeptides may be purified by affinity chromatography, employing a protein A or protein G column that will bind the Fc moieties.

The present invention provides isolated DNA sequences encoding 2F1 polypeptides fused to immunoglobin-derived polypeptides. Such DNA sequences may encode a soluble 2F1 fused to an antibody Fc region polypeptide, for example. DNA sequences encoding fusion proteins comprising multiple 2F1 polypeptide moieties are also encompassed by the present invention.

Compositions Comprising 2F1

The present invention provides compositions (including pharmaceutical compositions) comprising an effective amount of a purified 2F1 polypeptide and a suitable diluent, excipient, or carrier. 2F1 polypeptides administered in vivo preferably are in the form of a pharmaceutical composition.

The compositions of the present invention may contain a 2F1 protein in any form described herein, including oligomers, variants, derivatives, and biologically active fragments. In one embodiment of the invention, the composition comprises a soluble human 2F1 protein.

2F1 proteins may be formulated according to known methods that are used to prepare pharmaceutically useful compositions. Components that are commonly employed in pharmaceutical formulations include those described in *Remington's Pharmaceutical Sciences,* 16th ed., 1980, Mack Publishing Company.

2F1 protein employed in a pharmaceutical composition preferably is purified such that the 2F1 protein is substantially free of other proteins of natural or endogenous origin, desirably containing less than about 1% by mass of protein contaminants residual of production processes. Such compositions, however, can contain other proteins added as stabilizers, carriers, excipients or co-therapeutics.

Components of the compositions will be nontoxic to patients at the dosages and concentrations employed. Ordinarily, the preparation of such compositions entails combining a mammalian 2F1 polypeptide or derivative thereof with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent.

For therapeutic use, the compositions are administered in a manner and dosage appropriate to the indication and the patient. Administration may be by any suitable route, including but not limited to continuous infusion, local administration, sustained release from implants (gels, membranes, and the like), or intravenous injection.

Antibodies that Specifically Bind 2F1

The 2F1 proteins of the present invention, or immunogenic fragments thereof, may be employed in generating antibodies. The present invention thus provides antibodies that specifically bind 2F1, i.e., the antibodies bind to 2F1 via the antigen-binding sites of the antibody (as opposed to non-specific binding).

Polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988). Production of monoclonal antibodies that are immunoreactive with 2F1 is further illustrated in example 8 below.

Antigen-binding fragments of such antibodies, which may be produced using conventional techniques, are also encompassed by the present invention. Examples of such fragments include, but are not limited to, Fab, F(ab'), and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al. (*Bio/Technology* 7:934, 1989), and Winter and Harris (*TIPS* 14:139, May, 1993).

Among the uses of the antibodies is use in assays to detect the presence of 2F1 polypeptides, either in vitro or in vivo. The antibodies find further use in purifying 2F1 by immunoaffinity chromatography. Those antibodies that additionally can block transduction of a biological signal through 2F1 may be used to inhibit a biological activity mediated by such signal transduction. Disorders mediated or exacerbated (directly or indirectly) by signaling through 2F1 are thus treated. A therapeutic method involves in vivo administration of an amount of such an antibody that is effective in inhibiting an undesired 2F1-mediated biological activity. Such antibodies may be administered to inhibit prostaglandin synthesis, thereby treating one of the above-described prostaglandin-mediated disorders, for example.

Pharmaceutical compositions comprising an antibody that is directed against 2F1, and a suitable, diluent, excipient, or carrier, are provided herein. Suitable components of such compositions are as described above for compositions containing 2F1 proteins.

Conjugates comprising a diagnostic (detectable) or therapeutic agent attached to the above-described antibodies are provided herein. In one embodiment, the agent is a radionuclide or drug. Techniques for attaching such agents to antibodies are well known.

Expression Systems

The present invention provides recombinant expression vectors for expression of 2F1, and host cells transformed with the expression vectors. Any suitable expression system may be employed. The vectors include an 2F1 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the 2F1 DNA sequence. Thus, a promoter is operably linked to an 2F1 DNA sequence if the promoter controls the transcription of the 2F1 DNA sequence. An origin of replication, which confers the ability to replicate in the desired host cells, and a selection gene by which transformants are identified, are generally incorporated into the expression vector.

In addition, sequences encoding appropriate signal peptides that are not native to the 2F1 gene can be incorporated into expression vectors. For example, a DNA sequence for a signal peptide (secretory leader) may be fused in frame to the 5' end of an 2F1 sequence. A signal peptide that is functional in the intended host cells enhances extracellular secretion of the 2F1 polypeptide. The signal peptide is cleaved from the 2F1 polypeptide upon secretion of 2F1 from the cell.

Suitable host cells for expression of 2F1 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce 2F1 polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, an 2F1 polypeptide may include an N-terminal methionine residue to facilitate expression of the recombinant polypeptide in the prokaryotic host cell. The N-terminal Met may be cleaved from the expressed recombinant 2F1 polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and an 2F1 DNA sequence are inserted into the pBR322 vector.

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9 (ATCC 37092)) and pPLc28 (resident in *E. coli* RR1 (ATCC 53082)).

2F1 alternatively may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene.

Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the 2F1 polypeptide. The α-factor leader sequence is inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant 2F1 polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include COS cells derived from monkey kidney cells (e.g., the COS-1 cell line ATCC CRL 1650, or the COS-7 line ATCC CRL 1651, Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 by sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al. (*Nature* 312:768, 1984) has been deposited as ATCC 39890. Additional mammalian expression vectors are pDC406 (McMahan et al., *EMBO J.* 10:2821, 1991); HAV-EO (Dower et al., *J. Immunol.* 142:4314, 1989); pDC201 (Sims et al., *Science* 241:585, 1988); pDC302 (Mosley et al., *Cell,* 59:335, 1989); and those described in U.S. Pat. No. 5,350,683. Other suitable vectors may be derived from retroviruses.

In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Nucleic Acids and Uses Thereof

The 2F1-encoding DNAs disclosed herein find use in the production of 2F1 polypeptides, as discussed above. DNA and RNA complements of the DNA presented in SEQ ID NOS:1 and 3 are provided herein, along with both single-stranded and double-stranded forms thereof. Fragments of the 2F1 nucleotide sequences presented herein are also useful. Such fragments desirably comprise at least about 17 contigous nucleotides of the sequence presented in SEQ ID NO:1 or SEQ ID NO:3, or the complement thereof.

Among the uses of such 2F1 nucleic acids (including fragments) is use as a probe. Such probes may be employed in cross-species hybridization procedures to isolate 2F1 DNA from additional mammalian species. As one example, a probe corresponding to the extracellular domain of 2F1 may be employed. The probes also find use in detecting the presence of 2F1 nucleic acids in in vitro assays and in such procedures as Northern and Southern blots. Cell types expressing 2F1 can be identified. Such procedures are well known, and the skilled artisan can choose a probe of suitable length, depending on the particular intended application. The probes may be labeled (e.g., with $^{32}$P) by conventional techniques.

2F1 nucleic acid fragments also find use as primers in polymerase chain reactions (PCR). 5' and 3' primers corresponding to the termini of a desired 2F1 DNA may be employed in isolating and amplifying the DNA, using conventional PCR techniques.

Other useful fragments of the 2F1 nucleic acids are antisense or sense oligonucleotides comprising a single-stranded nucleic acid sequence (either RNA or DNA) capable of binding to target 2F1 mRNA (sense) or 2F1 DNA (antisense) sequences. Antisense or sense oligonucleotides, according to the present invention, comprise a fragment of the coding region of 2F1 cDNA. Such a fragment generally comprises at least about 14 nucleotides, preferably from about 14 to about 30 nucleotides. The ability to create an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of 2F1 proteins.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retroviral vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments, and not to limit the scope of the invention.

Example 1

Isolation of cDNA Encoding Human 2F1

A human 2F1 DNA was isolated by polymerase chain reaction (PCR). The primers employed in the reaction were degenerate oligonucleotides based on two regions within the cytoplasmic domain of the type I IL-1R. These two regions are among the motifs that are conserved in the IL-1 receptor family.

Initially, appropriate conditions for PCR amplification with the degenerate primers were determined by using human and mouse type I IL-1 receptors and mouse T1/ST2 cDNA clones as template. Using the conditions that were determined to yield an amplification product from each of these cDNAs, PCR was conducted using a 500 kb human yeast artificial chromosome (YAC) as template. This YAC, designated CO2133, contains DNA from the human chromosome 2q12 region and is known to include the type I IL-1 receptor, part of the type II IL-1 receptor, and ST2 (Sims et al., *Cytokine* 7:483-490, 1995).

The polymerase chain reactions (20 µl) employed 0.5 µl of a 16:1 mixture of Taq (Perkin-Elmer) and Vent (New England Biolabs) DNA polymerases and contained 200 pmole of each primer, 200 µM dNTPs and 5-10 µl of human YAC C02133 DNA, partially purified by extraction from a pulse-field gel. Cycle conditions were: 5 minutes at 94° C., during which time the DNA polymerase mixture was added; 40 cycles of (1 minute at 94° C., 3 minutes at 35° C., 1 minute at 72° C.); followed by 10 minutes at 72° C. The reaction products were separated by electrophoresis on a low-melting temperature agarose gel. The band containing material between 90 and 150 bp in length was excised, melted, and 5 µl used as template in a second PCR. The second reaction was performed similarly to the first, except that only 20 cycles were run. The reaction products were separated by electrophoresis on an agarose gel. The 90-150 bp fraction was eluted, and the DNA was rendered blunt-ended using T4 DNA polymerase, phosphorylated using T4 polynucleotide kinase, heated for 10 minutes at 65° C., ethanol precipitated, and ligated into a vector designated pCRScript (Stratagene Cloning Systems, La Jolla, Calif.) in the presence of restriction enzyme SrfI.

*E. coli* DH10 cells were transformed with the ligation products. White colonies were picked from XgaI plates, their inserts amplified by PCR using vector primers, and a small amount spotted on nylon filters. The filters were subsequently hybridized at 42° C. in aqueous conditions to a mixture of $^{32}$P-labelled oligonucleotide probes derived from human and murine type I IL-1R. Filters were washed at 50° C. in 0.3M NaCl. The hybridization thus was conducted under conditions of relatively low stringency.

Only 5 out of 180 inserts hybridized. Random DNA sequencing of 9 of the non-hybridizing inserts revealed that they were derived from yeast DNA. One of the five hybridizing inserts gave a strong hybridization signal, and DNA sequencing revealed it to be amplified from the type I IL-1R gene. Of the four weakly hybridizing inserts, three came from yeast DNA, and one was found to represent a novel gene, which has been designated 2F1.

The thus-isolated 2F1 DNA fragment was used to probe a cDNA library prepared from human peripheral blood lymphocytes (PBL), in an effort to isolate a full-length cDNA clone. Hybridizing clones were identified, and three 2F1 cDNA clones were isolated from the PBL library. Four additional 2F1 clones were isolated by PCR from the human epidermal carcinoma line KB (ATCC CCL 17).

A human 2F1 DNA sequence was elucidated by sequencing these clones. The nucleotide sequence of the coding region is presented in SEQ ID NO:1, and the amino acid sequence encoded thereby is presented in SEQ ID NO:2. The protein of SEQ ID NO:2 is a type I transmembrane protein, with an N-terminal signal peptide (amino acids −19 to −1) followed by an extracellular domain (amino acids 1 to 329), a transmembrane region (amino acids 330 to 351) and a cytoplasmic domain (amino acids 352 to 541). The codon for alanine 298 is polymorphic, being present in the PBL clones and two of the KB clones, and absent from the other two KB clones.

Example 2

Isolation of Murine 2F1 cDNA cDNA encoding murine 2F1 was isolated by cross-species hybridization, as follows. Human 2F1 cDNA was used as a probe to screen a mouse cDNA library derived from the cell line designated EL4 6.1 (MacDonald et al., *J. Immunol.* 135: 3944, 1985), which is a subclone of the thymoma cell line EL4 (ATCC TIB 39). A hybridizing clone was isolated. The nucleotide sequence of this mouse 2F1 cDNA and the amino acid sequence encoded thereby are presented in SEQ ID NO:3 and SEQ ID NO:4.

The protein of SEQ ID NO:4 comprises a signal peptide (amino acids −18 to −1), an extracellular domain (amino acids 1 to 307), a transmembrane region (amino acids 308 to 330), and a cytoplasmic domain (amino acids 331 to 519). The mouse 2F1 amino acid sequence of SEQ ID NO:4 is 65% identical to the human 2F1 amino acid sequence presented in SEQ ID NO:2.

Example 3

Binding Assay

2F1 is a member of the IL-1 receptor family, as discussed above. Since the 2F1 extracellular domain resembles that of the type I and type II IL-1 receptors, the ability of 2F1 to bind to IL-1 family members was investigated, as follows.

2F1 was tested for the ability to bind IL-1α and IL-1β (March et al. *Nature (Lond.)* 315:641, 1985), as well as IL-1 receptor antagonist protein (Eisenberg et al. *Nature* 343:341, 1990; Hannum et al., *Nature* 343:336, 1990; and Carter et al., *Nature* 344:633, 1990). IL-1 receptor antagonist (IL-1ra) binds to IL-1 receptors, but does not transduce a signal. By competing with IL-1 for binding to endogenous IL-1 receptors, IL-1ra inhibits biological effects mediated by IL-1.

A soluble fusion protein designated 2F1/Fc, which comprises the human 2F1 extracellular domain joined to the Fc region of a human IgG1, was generated by procedures analogous to those described in Baum et al. (*EMBO J.* 13:3992-4001, 1994). A soluble type I IL-1R/Fc fusion protein comprising the extracellular domain of human type I IL-1R fused to the Fc region polypeptide was prepared for use as a positive control.

A BIAcore biosensor (Pharmacia Biosensor AB, Piscataway, N.J.) was used to examine binding of IL-1 ligands to the human 2F1/Fc fusion protein, using procedures essentially as described in Arend et al. (*J. Immunol.* 153: 4766-4774, 19.

Briefly, a goat anti-human IgG serum directed against the Fc region (Jackson Immunoresearch Laboratories, Inc., West Grove, Pa.), covalently coupled to the dextran matrix of a hydrogel chip, was used to capture the human 2F1/Fc protein. The 2F1/Fc fusion protein thus was immobilized on the BIAcore chip. The three IL-1 ligands, at several different concentrations, were reacted with the captured protein, and the change of mass per unit area over time was measured.

The biosensor analysis demonstrated easily measurable binding of human IL-1α, IL-1β, and 1L-1ra to the human type I IL-1R/Fc fusion protein (positive control). However, no binding of any of the three IL-1 proteins to the 2F1/Fc fusion protein was detected. Thus, despite its significant sequence homology, 2F1 is not an IL-1 receptor.

Example 4

Northern Blot Analysis

The presence of 2F1 mRNA in various cell types was investigated by Northern blot analysis, using standard techniques. Northern blots purchased from Clonetech, Palo Alto, Calif., which contain 2 mg of human polyA$^+$ RNA in each lane, were probed overnight with a $^{32}$P-labeled antisense 2F1 riboprobe at 63° C. in 0.75M NaCl/50% formamide, and washed at 63° C. in 0.3M NaCl. To ascertain evenness of loading as well as effectiveness of rRNA removal, the filters were subsequently probed for GAPDH and 28S rRNA.

A single hybridizing band, migrating with or slightly faster than 28S rRNA, was found in spleen, thymus, leukocyte, liver, lung, heart, small and large intestine, prostate and placenta. It is possible, but uncertain, that a weak signal was seen in testis and ovary. No hybridizing band was detected in brain, skeletal muscle, kidney, and pancreas.

Example 5

Signaling Assay

The signal transduction capability of the 2F1 cytoplasmic domain was investigated in the following assay. An expression vector encoding a chimeric receptor, in which the extracellular and transmembrane portions of the mouse type I IL-1 receptor (IL-1RI) were fused to the cytoplasmic portion of the human 2F1, was constructed. The vector encoded amino acids 1 to 362 of the murine IL-1RI fused to amino acids 332 to 522 of human 2F1. In preparing the construct, a BglII site was introduced into the murine IL-1RI DNA, just 3' of the transmembrane region. This resulted in the valine residue at position 361 of the murine IL-1RI being changed to isoleucine, which is the amino acid present in the human IL-1RI at that position.

Use of the chimeric receptor made it possible to assay for response to a known ligand (IL-1). When cells expressing IL-1RI are contacted with IL-1α or IL-1β, a number of responses are induced, including stimulation of nuclear localization of the transcription factor NF-κB (Thanos, D. and T. Maniatis, Cell 80:529-532, 1995). Activated NF-κB complexes translocate to the nucleus and bind the cognate recognition sequence.

The chimeric receptor was expressed in COS-7 cells (ATCC CRL 1651), and the ability of IL-1 to activate the transcription factor NF-κB was examined in an NF-κB gel assay. A sheep anti-human IL-1RI polyclonal antiserum (designated P3 herein) was used to block the endogenous (cross-reactive) monkey IL-1R, without affecting IL-1 binding to the transfected murine IL-1RI/2F1 chimera. COS-7 cells transfected with an expression vector encoding the extracellular and transmembrane portions of the murine IL-1RI, but no cytoplasmic domain, were employed as a negative control. As a positive control, COS-7 cells were transfected with an expression vector encoding full length murine IL-1RI.

The assay procedure was as follows. COS-7 cells were transfected with the receptor constructs. Two days post-transfection, cells were treated with the blocking antibody and stimulated (30 minutes, 1 ng/ml) with human IL-1α. Immediately after the blocking and IL-1 stimulation, nuclear extracts were prepared from cell samples, essentially as described by Ostrowski et al. (J. Biol. Chem. 266:12722-33, 1991). A double-stranded synthetic oligonucleotide probe containing the KB enhancer element from the immunoglobulin k light chain was 5' end labelled by phosphorylation with [γ-$^{32}$P]ATP. The nuclear extracts (10 μg) were incubated with the $^{32}$P-labeled probe for 20 minutes at room temperature, and protein-DNA complexes then were resolved by electrophoresis in 0.5×TBE 10% polyacrylamide gels (Novex). NF-κB complexed with DNA indicates NF-κB activation.

The 2F1 cytoplasmic domain was found to induce NF-κB DNA binding ability, in response to IL-1 stimulation of the chimeric receptor molecule. The induction was comparable in magnitude to that mediated via the murine IL-1RI (positive control).

Example 6

Signaling Assay

The signalling capability of 2F1 was examined further in an interleukin-8 (IL-8) promoter activation assay. When cells expressing the type I IL-1R are contacted with IL-1, transcription of the IL-8 gene is stimulated (Mukaida et al., J. Biol. Chem. 265:21128-33, 1990). The IL-1R/2F1 chimeric receptor described in example 5 was employed in this assay, so that response to a known ligand (IL-1) could be investigated.

A reporter plasmid designated pIL8p, carrying a partial human IL-8 promoter fused to the coding region of the human IL-2 receptor alpha chain, was prepared. COS7 cells (1×10$^5$ cells per well in a 12-well tissue culture plate) were co-transfected with 1500 ng of pIL8p and 500 ng of an expression vector encoding the IL-1R/2F1 chimeric receptor. Twenty-four hours post-transfection, the culture medium was changed and the cells were contacted with a blocking antibody, then stimulated with 1 ng/ml human IL-1α or left unstimulated. The blocking antibody was a 1:100 dilution of the sheep anti-human IL-1RI polyclonal serum P3 see example 5), which at that concentration blocks binding of IL-1 to the endogenous COS7 cell IL-1 receptors, but has no effect on binding of IL-1 to the mouse IL-1RI portion of the recombinant chimeric receptor.

Twelve to sixteen hours post-stimulation, cells were washed twice with binding medium containing 5% (w/v) non-fat dry milk (5% MBM), and blocked with 2 ml 5% MBM at room temperature for 30 minutes. Cell were then incubated at room temperature for 60-90 minutes with 1.5 mls/well of 5% MBM containing 1 μg/ml of mouse monoclonal antibody 2A3 directed against IL-2Rα (Cosman et al., Nature 312:768-771, 1984), with gentle rocking. Cells were washed with 5% MBM, then incubated for one hour at room temperature with 1 ml/well of 5% MBM containing a 1:100 dilution of [$^{125}$I]goat anti-mouse IgG (Sigma Chemical Company, St. Louis, Mo.). Wells were washed four times with 5% MBM, twice with PBS, then stripped by adding 1 ml 0.5 M NaOH, and the counts per minute determined.

The IL-1R/2F1 chimeric receptor was found to respond to IL-1α by induction of IL-8 promoter function. Transcription of the reporter construct was induced by IL-1 stimulation of the IL-1R/2F1 chimera, to about half the level mediated by the intact mouse type I IL-1R.

Example 7

Prostaglandin Synthesis

In a third assay, the IL-1R/2F1 chimeric receptor was expressed in KB human epidermal carcinoma cells (ATCC CCL 17). In the presence of polyclonal antiserum that blocks human type I IL-1 receptors (see example 5), IL-1 stimulation of the chimeric receptor resulted in the synthesis of prostaglandin $E_2$.

Example 8

Monoclonal Antibodies Directed Against 2F1

This example illustrates the preparation of monoclonal antibodies that are immunoreactive with a 2F1 protein. Human 2F1 is expressed in mammalian host cells, such as COS-7 or CV-1/EBNA-1 cells. The expressed 2F1 is purified and employed as an immunogen in generating monoclonal antibodies, using conventional techniques such as those described in U.S. Pat. No. 4,411,993. Alternative immunogens include, but are not limited to, 2F1 fragments (e.g., soluble 2F1 comprising the extracellular domain), a soluble 2F1/Fc fusion protein, or cells expressing recombinant 2F1 on the cell surface.

Briefly, mice are immunized with 2F1 emulsified in complete Freund's adjuvant and injected subcutaneously or intraperitoneally in amounts ranging from 10-100 μg. Ten to twelve days later, the immunized animals are boosted with additional 2F1 emulsified in incomplete Freund's adjuvant. Mice are boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for 2F1 antibodies.

Following detection of an appropriate antibody titer, positive animals are provided one last intravenous injection of 2F1 in saline. Three to four days later, the animals are sacrificed, and spleen cells are harvested and fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified 2F1 by adaptations of the techniques disclosed in Engvall et al. (*Immunochem.* 8:871, 1971) and in U.S. Pat. No. 4,703,004. A preferred screening technique is the antibody capture technique described in Beckmann et al. (*J. Immunol.* 144:4212, 1990). Positive hybridoma cells can be injected intraperitoneally into syngeneic BALB/c mice to produce ascites containing high concentrations of anti-2F1 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to 2F1.

What is claimed is:

1. A method of treating an inflammatory disorder of the lungs, the method comprising administering to a patient an effective amount of a composition comprising an antibody specific for a polypeptide consisting of an amino acid sequence selected from the group consisting of:

(a) −19 to 522 of SEQ ID NO:2;
(b) 1 to 522 of SEQ ID NO:2;
(c) −19 to 310 of SEQ ID NO:2;
(d) 1 to 310 of SEQ ID NO:2 and
(e) the amino acid sequence set forth in any one of a)-d) above, with the exception that amino acid 298 is deleted, wherein the inflammatory disorder of the lungs is an inflammatory disorder of the lung associated with allergy, an inflammatory disorder of the lung associated with asthma, or adult respiratory distress syndrome.

2. The method of claim 1, wherein the antibody is specific for a polypeptide consisting of the amino acid sequence of −19 to 522 of SEQ ID NO:2.

3. The method of claim 1, wherein the antibody is specific for a polypeptide consisting of the amino acid sequence of −19 to 522 of SEQ ID NO:2 with the exception that amino acid 298 is deleted.

4. The method of claim 1, wherein the antibody is specific for a polypeptide consisting of the amino acid sequence of 1 to 522 of SEQ ID NO:2.

5. The method of claim 1, wherein the antibody is specific for a polypeptide consisting of the amino acid sequence of 1 to 522 of SEQ ID NO:2 with the exception that amino acid 298 is deleted.

6. The method of claim 1, wherein the antibody is specific for a polypeptide consisting of the amino acid sequence of −19 to 310 of SEQ ID NO:2.

7. The method of claim 1, wherein the antibody is specific for a polypeptide consisting of the amino acid sequence of −19 to 310 of SEQ ID NO:2 with the exception that amino acid 298 is deleted.

8. The method of claim 1, wherein the antibody is specific for a polypeptide consisting of the amino acid sequence of 1 to 310 of SEQ ID NO:2.

9. The method of claim 1, wherein the antibody is specific for a polypeptide consisting of the amino acid sequence of 1 to 310 of SEQ ID NO:2 with the exception that amino acid 298 is deleted.

10. The method of claim 1, wherein the inflammatory disorder of the lungs is associated with allergy.

11. The method of claim 1, wherein the inflammatory disorder of the lungs is associated with asthma.

12. The method of claim 1, wherein the inflammatory disorder of the lungs is adult respiratory distress syndrome.

13. A method of treating an inflammatory disorder of the lungs, the method comprising administering to a patient an effective amount of a composition comprising a monoclonal antibody specific for a polypeptide consisting of an amino acid sequence selected from the group consisting of:
  (a) −19 to 522 of SEQ ID NO:2;
  (b) 1 to 522 of SEQ ID NO:2;
  (c) −19 to 310 of SEQ ID NO:2;
  (d) 1 to 310 of SEQ ID NO:2 and
  (e) the amino acid sequence set forth in any one of a)-d) above, with the exception that amino acid 298 is deleted;
  wherein the inflammatory disorder of the lungs is an inflammatory disorder of the lung associated with allergy, an inflammatory disorder of the lung associated with asthma, or adult respiratory distress syndrome.

14. The method of claim 13, wherein the monoclonal antibody is specific for a polypeptide consisting of the amino acid sequence of −19 to 522 of SEQ ID NO:2.

15. The method of claim 13, wherein the monoclonal antibody is specific for a polypeptide consisting of the amino acid sequence of −19 to 522 of SEQ ID NO:2 with the exception that amino acid 298 is deleted.

16. The method of claim 13, wherein the monoclonal antibody is specific for a polypeptide consisting of the amino acid sequence of 1 to 522 of SEQ ID NO:2.

17. The method of claim 13, wherein the monoclonal antibody is specific for a polypeptide consisting of the amino acid sequence of 1 to 522 of SEQ ID NO:2 with the exception that amino acid 298 is deleted.

18. The method of claim 13, wherein the monoclonal antibody is specific for a polypeptide consisting of the amino acid sequence of −19 to 310 of SEQ ID NO:2.

19. The method of claim 13, wherein the monoclonal antibody is specific for a polypeptide consisting of the amino acid sequence of −19 to 310 of SEQ ID NO:2 with the exception that amino acid 298 is deleted.

20. The method of claim 13, wherein the monoclonal antibody is specific for a polypeptide consisting of the amino acid sequence of 1 to 310 of SEQ ID NO:2.

21. The method of claim 13, wherein the monoclonal antibody is specific for a polypeptide consisting of the amino acid sequence of 1 to 310 of SEQ ID NO:2 with the exception that amino acid 298 is deleted.

22. The method of claim 13, wherein the inflammatory disorder of the lungs is associated with allergy.

23. The method of claim 13, wherein the inflammatory disorder of the lungs is associated with asthma.

24. The method of claim 13, wherein the inflammatory disorder of the lungs is adult respiratory distress syndrome.

* * * * *

SEQUENCE LISTING

```
<160> NUMBER OF SEQ ID NOS: 5

<210> SEQ ID NO 1
<211> LENGTH: 1626
<212> TYPE: DNA
<213> ORGANISM: Homo sapiens
<220> FEATURE:
<221> NAME/KEY: CDS
<222> LOCATION: (1)..(1623)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1623)

<400> SEQUENCE: 1 atg aat tgt aga gaa tta ccc ttg acc ctt tgg gtg ctt ata tct gta      48
Met Asn Cys Arg Glu Leu Pro Leu Thr Leu Trp Val Leu Ile Ser Val
            -15                 -10                 -5 agc act gca gaa tct tgt act tca cgt ccc cac att act gtg gtt gaa      96
Ser Thr Ala Glu Ser Cys Thr Ser Arg Pro His Ile Thr Val Val Glu
        -1   1               5                  10 ggg gaa cct ttc tat ctg aaa cat tgc tcg tgt tca ctt gca cat gag     144
Gly Glu Pro Phe Tyr Leu Lys His Cys Ser Cys Ser Leu Ala His Glu
        15                  20                  25 att gaa aca acc acc aaa agc tgg tac aaa agc agt gga tca cag gaa     192
Ile Glu Thr Thr Thr Lys Ser Trp Tyr Lys Ser Ser Gly Ser Gln Glu
30                  35                  40                  45
```

```
cat gtg gag ctg aac cca agg agt tcc tcg aga att gct ttg cat gat       240
His Val Glu Leu Asn Pro Arg Ser Ser Ser Arg Ile Ala Leu His Asp
             50                  55                  60 tgt gtt ttg gag ttt tgg cca gtt gag ttg aat gac aca gga tct tac       288
Cys Val Leu Glu Phe Trp Pro Val Glu Leu Asn Asp Thr Gly Ser Tyr
 65                  70                  75 ttt ttc caa atg aaa aat tat act cag aaa tgg aaa tta aat gtc atc       336
Phe Phe Gln Met Lys Asn Tyr Thr Gln Lys Trp Lys Leu Asn Val Ile
         80                  85                  90 aga aga aat aaa cac agc tgt ttc act gaa aga caa gta act agt aaa       384
Arg Arg Asn Lys His Ser Cys Phe Thr Glu Arg Gln Val Thr Ser Lys
 95                 100                 105 att gtg gaa gtt aaa aaa ttt ttt cag ata acc tgt gaa aac agt tac       432
Ile Val Glu Val Lys Lys Phe Phe Gln Ile Thr Cys Glu Asn Ser Tyr
110                 115                 120                 125 tat caa aca ctg gtc aac agc aca tca ttg tat aag aac tgt aaa aag       480
Tyr Gln Thr Leu Val Asn Ser Thr Ser Leu Tyr Lys Asn Cys Lys Lys
                130                 135                 140 cta cta ctg gag aac aat aaa aac cca acg ata aag aag aac gcc gag       528
Leu Leu Leu Glu Asn Asn Lys Asn Pro Thr Ile Lys Lys Asn Ala Glu
            145                 150                 155 ttt gaa gat cag ggg tat tac tcc tgc gtg cat ttc ctt cat cat aat       576
Phe Glu Asp Gln Gly Tyr Tyr Ser Cys Val His Phe Leu His His Asn
        160                 165                 170 gga aaa cta ttt aat atc acc aaa acc ttc aat ata aca ata gtg gaa       624
Gly Lys Leu Phe Asn Ile Thr Lys Thr Phe Asn Ile Thr Ile Val Glu
175                 180                 185 gat cgc agt aat ata gtt ccg gtt ctt ctt gga cca aag ctt aac cat       672
Asp Arg Ser Asn Ile Val Pro Val Leu Leu Gly Pro Lys Leu Asn His
190                 195                 200                 205 gtt gca gtg gaa tta gga aaa aac gta agg ctc aac tgc tct gct ttg       720
Val Ala Val Glu Leu Gly Lys Asn Val Arg Leu Asn Cys Ser Ala Leu
                210                 215                 220 ctg aat gaa gag gat gta att tat tgg atg ttt ggg gaa gaa aat gga       768
Leu Asn Glu Glu Asp Val Ile Tyr Trp Met Phe Gly Glu Glu Asn Gly
            225                 230                 235 tcg gat cct aat ata cat gaa gag aaa gaa atg aga att atg act cca       816
Ser Asp Pro Asn Ile His Glu Glu Lys Glu Met Arg Ile Met Thr Pro
        240                 245                 250 gaa ggc aaa tgg cat gct tca aaa gta ttg aga att gaa aat att ggt       864
Glu Gly Lys Trp His Ala Ser Lys Val Leu Arg Ile Glu Asn Ile Gly
255                 260                 265 gaa agc aat cta aat gtt tta tat aat tgc act gtg gcc agc acg gga       912
Glu Ser Asn Leu Asn Val Leu Tyr Asn Cys Thr Val Ala Ser Thr Gly
270                 275                 280                 285 ggc aca gac acc aaa agc ttc atc ttg gtg aga aaa gca gac atg gct       960
Gly Thr Asp Thr Lys Ser Phe Ile Leu Val Arg Lys Ala Asp Met Ala
                290                 295                 300 gat atc cca ggc cac gtc ttc aca aga gga atg atc ata gct gtt ttg      1008
Asp Ile Pro Gly His Val Phe Thr Arg Gly Met Ile Ile Ala Val Leu
            305                 310                 315 atc ttg gtg gca gta gtg tgc cta gtg act gtg tgt gtc att tat aga      1056
Ile Leu Val Ala Val Val Cys Leu Val Thr Val Cys Val Ile Tyr Arg
        320                 325                 330 gtt gac ttg gtt cta ttt tat aga cat tta acg aga aga gat gaa aca      1104
Val Asp Leu Val Leu Phe Tyr Arg His Leu Thr Arg Arg Asp Glu Thr
335                 340                 345 tta aca gat gga aaa aca tat gat gct ttt gtg tct tac cta aaa gaa      1152
Leu Thr Asp Gly Lys Thr Tyr Asp Ala Phe Val Ser Tyr Leu Lys Glu
350                 355                 360                 365
```

```
tgc cga cct gaa aat gga gag gag cac acc ttt gct gtg gag att ttg      1200
Cys Arg Pro Glu Asn Gly Glu Glu His Thr Phe Ala Val Glu Ile Leu
            370                 375                 380 ccc agg gtg ttg gag aaa cat ttt ggg tat aag tta tgc ata ttt gaa      1248
Pro Arg Val Leu Glu Lys His Phe Gly Tyr Lys Leu Cys Ile Phe Glu
        385                 390                 395 agg gat gta gtg cct gga gga gct gtt gtt gat gaa atc cac tca ctg      1296
Arg Asp Val Val Pro Gly Gly Ala Val Val Asp Glu Ile His Ser Leu
    400                 405                 410 ata gag aaa agc cga aga cta atc att gtc cta agt aaa agt tat atg      1344
Ile Glu Lys Ser Arg Arg Leu Ile Ile Val Leu Ser Lys Ser Tyr Met
415                 420                 425 tct aat gag gtc agg tat gaa ctt gaa agt gga ctc cat gaa gca ttg      1392
Ser Asn Glu Val Arg Tyr Glu Leu Glu Ser Gly Leu His Glu Ala Leu
430                 435                 440                 445 gtg gaa aga aaa att aaa ata atc tta att gaa ttt aca cct gtt act      1440
Val Glu Arg Lys Ile Lys Ile Ile Leu Ile Glu Phe Thr Pro Val Thr
                450                 455                 460 gac ttc aca ttc ttg ccc caa tca cta aag ctt tgg aaa tct cac aga      1488
Asp Phe Thr Phe Leu Pro Gln Ser Leu Lys Leu Trp Lys Ser His Arg
            465                 470                 475 gtt ctg aag tgg aag gcc gat aaa tct ctt tct tat aac tca agg ttc      1536
Val Leu Lys Trp Lys Ala Asp Lys Ser Leu Ser Tyr Asn Ser Arg Phe
        480                 485                 490 tgg aag aac ctt ctt tac tta atg cct gca aaa aca gtc aag cca ggt      1584
Trp Lys Asn Leu Leu Tyr Leu Met Pro Ala Lys Thr Val Lys Pro Gly
    495                 500                 505 aga gac gaa ccg gaa gtc ttg cct gtt ctt tcc gag tct taa              1626
Arg Asp Glu Pro Glu Val Leu Pro Val Leu Ser Glu Ser
510                 515                 520

<210> SEQ ID NO 2
<211> LENGTH: 541
<212> TYPE: PRT
<213> ORGANISM: Homo sapiens

<400> SEQUENCE: 2

Met Asn Cys Arg Glu Leu Pro Leu Thr Leu Trp Val Leu Ile Ser Val
                -15                 -10                 -5

Ser Thr Ala Glu Ser Cys Thr Ser Arg Pro His Ile Thr Val Val Glu
         -1   1              5                  10

Gly Glu Pro Phe Tyr Leu Lys His Cys Ser Cys Ser Leu Ala His Glu
             15                  20                  25

Ile Glu Thr Thr Thr Lys Ser Trp Tyr Lys Ser Gly Ser Gln Glu
 30                  35                  40                  45

His Val Glu Leu Asn Pro Arg Ser Ser Ser Arg Ile Ala Leu His Asp
                 50                  55                  60

Cys Val Leu Glu Phe Trp Pro Val Glu Leu Asn Asp Thr Gly Ser Tyr
             65                  70                  75

Phe Phe Gln Met Lys Asn Tyr Thr Gln Lys Trp Lys Leu Asn Val Ile
         80                  85                  90

Arg Arg Asn Lys His Ser Cys Phe Thr Glu Arg Gln Val Thr Ser Lys
     95                 100                 105

Ile Val Glu Val Lys Lys Phe Phe Gln Ile Thr Cys Glu Asn Ser Tyr
110                 115                 120                 125

Tyr Gln Thr Leu Val Asn Ser Thr Ser Leu Tyr Lys Asn Cys Lys Lys
                130                 135                 140

Leu Leu Leu Glu Asn Asn Lys Asn Pro Thr Ile Lys Lys Asn Ala Glu
            145                 150                 155
```

```
Phe Glu Asp Gln Gly Tyr Tyr Ser Cys Val His Phe Leu His His Asn
        160                 165                 170
Gly Lys Leu Phe Asn Ile Thr Lys Thr Phe Asn Ile Thr Ile Val Glu
    175                 180                 185
Asp Arg Ser Asn Ile Val Pro Val Leu Leu Gly Pro Lys Leu Asn His
190                 195                 200                 205
Val Ala Val Glu Leu Gly Lys Asn Val Arg Leu Asn Cys Ser Ala Leu
                210                 215                 220
Leu Asn Glu Glu Asp Val Ile Tyr Trp Met Phe Gly Glu Glu Asn Gly
            225                 230                 235
Ser Asp Pro Asn Ile His Glu Glu Lys Glu Met Arg Ile Met Thr Pro
        240                 245                 250
Glu Gly Lys Trp His Ala Ser Lys Val Leu Arg Ile Glu Asn Ile Gly
    255                 260                 265
Glu Ser Asn Leu Asn Val Leu Tyr Asn Cys Thr Val Ala Ser Thr Gly
270                 275                 280                 285
Gly Thr Asp Thr Lys Ser Phe Ile Leu Val Arg Lys Ala Asp Met Ala
                290                 295                 300
Asp Ile Pro Gly His Val Phe Thr Arg Gly Met Ile Ile Ala Val Leu
            305                 310                 315
Ile Leu Val Ala Val Val Cys Leu Val Thr Val Cys Val Ile Tyr Arg
        320                 325                 330
Val Asp Leu Val Leu Phe Tyr Arg His Leu Thr Arg Arg Asp Glu Thr
    335                 340                 345
Leu Thr Asp Gly Lys Thr Tyr Asp Ala Phe Val Ser Tyr Leu Lys Glu
350                 355                 360                 365
Cys Arg Pro Glu Asn Gly Glu Glu His Thr Phe Ala Val Glu Ile Leu
                370                 375                 380
Pro Arg Val Leu Glu Lys His Phe Gly Tyr Lys Leu Cys Ile Phe Glu
            385                 390                 395
Arg Asp Val Val Pro Gly Gly Ala Val Val Asp Glu Ile His Ser Leu
        400                 405                 410
Ile Glu Lys Ser Arg Arg Leu Ile Ile Val Leu Ser Lys Ser Tyr Met
    415                 420                 425
Ser Asn Glu Val Arg Tyr Glu Leu Glu Ser Gly Leu His Glu Ala Leu
430                 435                 440                 445
Val Glu Arg Lys Ile Lys Ile Ile Leu Ile Glu Phe Thr Pro Val Thr
                450                 455                 460
Asp Phe Thr Phe Leu Pro Gln Ser Leu Lys Leu Leu Lys Ser His Arg
            465                 470                 475
Val Leu Lys Trp Lys Ala Asp Lys Ser Leu Ser Tyr Asn Ser Arg Phe
        480                 485                 490
Trp Lys Asn Leu Leu Tyr Leu Met Pro Ala Lys Thr Val Lys Pro Gly
    495                 500                 505
Arg Asp Glu Pro Glu Val Leu Pro Val Leu Ser Glu Ser
510                 515                 520

<210> SEQ ID NO 3
<211> LENGTH: 2830
<212> TYPE: DNA
<213> ORGANISM: Homo sapiens
<220> FEATURE:
<221> NAME/KEY: CDS
<222> LOCATION: (381)..(1991)
<220> FEATURE:
<221> NAME/KEY: sig_peptide
```

<220> FEATURE:
<221> NAME/KEY: mat_peptide
<222> LOCATION: (435)..(1991)

<400> SEQUENCE: 3

```
tcccagccct ccacctccct accccccggtc gttggcttct tcttcttctt cttcttttt      60 tttttttcctg cgataattct ctggtttgcc aaatctctct aatcaagctc ctggccttgc     120
ctcactgtgc cttccctccc tgtctgttgt cacagttgtg gaccaggagg tatttagtct     180
cacttgctgg gcgaatcctg cttcacagat gtaagcgaag gagaagccac tgcccaggcc     240
tgtgtgtggg ccacctctct gaaggtaagg gcagactctg atgtccagtc ctcactgtct     300
tctgctgtct ggagcaagga gaggaaccac ccacaacgat cctgaaaaca agagatacca     360
ttcaaagtgg aagcctaaac atg cat cat gaa gaa tta atc ttg aca ctc tgc     413
                      Met His His Glu Glu Leu Ile Leu Thr Leu Cys
                                -15                  -10 att ctc att gtt aaa agt gcc tca aaa agt tgt att cac cga tca caa        461
Ile Leu Ile Val Lys Ser Ala Ser Lys Ser Cys Ile His Arg Ser Gln
         -5                  -1  1                   5 att cat gtg gta gag gga gaa cct ttt tat ctg aag cca tgt ggc ata        509
Ile His Val Val Glu Gly Glu Pro Phe Tyr Leu Lys Pro Cys Gly Ile
 10                  15                  20                  25 tct gca cca gtg cac agg aat gaa aca gcc acc atg aga tgg ttc aaa        557
Ser Ala Pro Val His Arg Asn Glu Thr Ala Thr Met Arg Trp Phe Lys
                 30                  35                  40 ggc agt gct tca cat gag tat aga gag ctg aac aac aga agc tcg ccc        605
Gly Ser Ala Ser His Glu Tyr Arg Glu Leu Asn Asn Arg Ser Ser Pro
             45                  50                  55 aga gtc act ttt cat gat cac acc ttg gaa ttc tgg cca gtt gag atg        653
Arg Val Thr Phe His Asp His Thr Leu Glu Phe Trp Pro Val Glu Met
         60                  65                  70 gag gat gag gga acg tac att tct caa gtc gga aat gat cgt cgc aat        701
Glu Asp Glu Gly Thr Tyr Ile Ser Gln Val Gly Asn Asp Arg Arg Asn
 75                  80                  85 tgg acc tta aat gtc acc aaa aga aac aaa cac agc tgt ttc tct gac        749
Trp Thr Leu Asn Val Thr Lys Arg Asn Lys His Ser Cys Phe Ser Asp
 90                  95                 100                 105 aag ctc gtg aca agc aga gat gtt gaa gtt aac aaa tct ctg cat atc        797
Lys Leu Val Thr Ser Arg Asp Val Glu Val Asn Lys Ser Leu His Ile
                110                 115                 120 act tgt aag aat cct aac tat gaa gag ctg atc cag gac aca tgg ctg        845
Thr Cys Lys Asn Pro Asn Tyr Glu Glu Leu Ile Gln Asp Thr Trp Leu
            125                 130                 135 tat aag aac tgt aag gaa ata tcc aaa acc cca agg atc ctg aag gat        893
Tyr Lys Asn Cys Lys Glu Ile Ser Lys Thr Pro Arg Ile Leu Lys Asp
        140                 145                 150 gcc gag ttt gga gat gag ggc tac tac tcc tgc gtg ttt tct gtc cac        941
Ala Glu Phe Gly Asp Glu Gly Tyr Tyr Ser Cys Val Phe Ser Val His
    155                 160                 165 cat aat ggg aca cgg tac aac atc acc aag act gtc aat ata aca gtt        989
His Asn Gly Thr Arg Tyr Asn Ile Thr Lys Thr Val Asn Ile Thr Val
170                 175                 180                 185 att gaa gga agg agt aaa gta act cca gct att tta gga cca aag tgt       1037
Ile Glu Gly Arg Ser Lys Val Thr Pro Ala Ile Leu Gly Pro Lys Cys
                190                 195                 200 gag aag gtt ggt gta gaa cta gga aag gat gtg gag ttg aac tgc agt       1085
Glu Lys Val Gly Val Glu Leu Gly Lys Asp Val Glu Leu Asn Cys Ser
            205                 210                 215 gct tca ttg aat aaa gac gat ctg ttt tat tgg agc atc agg aaa gag       1133
```

|  |  |  |  |  |  |  |  |  |  |  |  |  |  |  |
|---|---|---|---|---|---|---|---|---|---|---|---|---|---|---|
| Ala | Ser | Leu | Asn<br>220 | Lys | Asp | Asp | Leu<br>225 | Phe | Tyr | Trp | Ser<br>230 | Ile | Arg | Lys | Glu |

| gac | agc | tca | gac | cct | aat | gtg | caa | gaa | gac | agg | aag | gag | acg | aca | aca | 1181 |
|---|---|---|---|---|---|---|---|---|---|---|---|---|---|---|---|---|
| Asp | Ser | Ser | Asp<br>235 | Pro | Asn | Val | Gln<br>240 | Glu | Asp | Arg | Lys<br>245 | Glu | Thr | Thr | Thr |  |

| tgg | att | tct | gaa | ggc | aaa | ctg | cat | gct | tca | aaa | ata | ctg | aga | ttt | cag | 1229 |
|---|---|---|---|---|---|---|---|---|---|---|---|---|---|---|---|---|
| Trp<br>250 | Ile | Ser | Glu | Gly | Lys<br>255 | Leu | His | Ala | Ser | Lys<br>260 | Ile | Leu | Arg | Phe | Gln<br>265 |  |

| aaa | att | act | gaa | aac | tat | ctc | aat | gtt | tta | tat | aat | tgc | acc | gtg | gcc | 1277 |
|---|---|---|---|---|---|---|---|---|---|---|---|---|---|---|---|---|
| Lys | Ile | Thr | Glu | Asn<br>270 | Tyr | Leu | Asn | Val | Leu<br>275 | Tyr | Asn | Cys | Thr | Val<br>280 | Ala |  |

| aac | gaa | gaa | gcc | ata | gac | acc | aag | agc | ttc | gtc | ttg | gtg | aga | aaa | gaa | 1325 |
|---|---|---|---|---|---|---|---|---|---|---|---|---|---|---|---|---|
| Asn | Glu | Glu | Ala | Ile<br>285 | Asp | Thr | Lys | Ser | Phe<br>290 | Val | Leu | Val | Arg | Lys<br>295 | Glu |  |

| ata | cct | gat | atc | cca | ggc | cat | gtc | ttt | aca | gga | gga | gta | act | gtg | ctt | 1373 |
|---|---|---|---|---|---|---|---|---|---|---|---|---|---|---|---|---|
| Ile | Pro | Asp | Ile<br>300 | Pro | Gly | His | Val | Phe<br>305 | Thr | Gly | Gly | Val | Thr<br>310 | Val | Leu |  |

| gtt | ctc | gcc | tct | gtg | gca | gca | gtg | tgt | ata | gtg | att | ttg | tgt | gtc | att | 1421 |
|---|---|---|---|---|---|---|---|---|---|---|---|---|---|---|---|---|
| Val | Leu | Ala | Ser | Val<br>315 | Ala | Ala | Val | Cys | Ile<br>320 | Val | Ile | Leu | Cys | Val<br>325 | Ile |  |

| tat | aaa | gtt | gac | ttg | gtt | ctg | ttc | tat | agg | cgc | ata | gcg | gaa | aga | gac | 1469 |
|---|---|---|---|---|---|---|---|---|---|---|---|---|---|---|---|---|
| Tyr<br>330 | Lys | Val | Asp | Leu | Val<br>335 | Leu | Phe | Tyr | Arg | Arg<br>340 | Ile | Ala | Glu | Arg | Asp<br>345 |  |

| gag | aca | cta | aca | gat | ggt | aaa | aca | tat | gat | gcc | ttt | gtg | tct | tac | ctg | 1517 |
|---|---|---|---|---|---|---|---|---|---|---|---|---|---|---|---|---|
| Glu | Thr | Leu | Thr | Asp | Gly | Lys<br>350 | Thr | Tyr | Asp | Ala | Phe<br>355 | Val | Ser | Tyr | Leu<br>360 |  |

| aaa | gag | tgt | cat | cct | gag | aat | aaa | gaa | gag | tat | act | ttt | gct | gtg | gag | 1565 |
|---|---|---|---|---|---|---|---|---|---|---|---|---|---|---|---|---|
| Lys | Glu | Cys | His | Pro<br>365 | Glu | Asn | Lys | Glu | Glu<br>370 | Tyr | Thr | Phe | Ala | Val<br>375 | Glu |  |

| acg | tta | ccc | agg | gtc | ctg | gag | aaa | cag | ttt | ggg | tat | aag | tta | tgc | ata | 1613 |
|---|---|---|---|---|---|---|---|---|---|---|---|---|---|---|---|---|
| Thr | Leu | Pro | Arg<br>380 | Val | Leu | Glu | Lys | Gln<br>385 | Phe | Gly | Tyr | Lys | Leu<br>390 | Cys | Ile |  |

| ttt | gaa | aga | gat | gtg | gtg | cct | ggc | gga | gct | gtt | gtc | gag | gag | atc | cat | 1661 |
|---|---|---|---|---|---|---|---|---|---|---|---|---|---|---|---|---|
| Phe | Glu | Arg | Asp | Val<br>395 | Val | Pro | Gly | Gly | Ala<br>400 | Val | Val | Glu | Glu | Ile<br>405 | His |  |

| tca | ctg | ata | gag | aaa | agc | cgg | agg | cta | atc | atc | gtt | ctc | agc | cag | agt | 1709 |
|---|---|---|---|---|---|---|---|---|---|---|---|---|---|---|---|---|
| Ser | Leu | Ile | Glu<br>410 | Lys | Ser | Arg | Arg | Leu<br>415 | Ile | Ile | Val | Leu | Ser<br>420 | Gln | Ser<br>425 |  |

| tac | ctg | act | aac | gga | gcc | agg | cgt | gag | ctc | gag | agt | gga | ctc | cac | gaa | 1757 |
|---|---|---|---|---|---|---|---|---|---|---|---|---|---|---|---|---|
| Tyr | Leu | Thr | Asn | Gly<br>430 | Ala | Arg | Arg | Glu | Leu<br>435 | Glu | Ser | Gly | Leu | His<br>440 | Glu |  |

| gca | ctg | gta | gag | agg | aag | att | aag | atc | atc | tta | att | gag | ttt | act | cca | 1805 |
|---|---|---|---|---|---|---|---|---|---|---|---|---|---|---|---|---|
| Ala | Leu | Val | Glu | Arg | Lys<br>445 | Ile | Lys | Ile | Ile | Leu<br>450 | Ile | Glu | Phe | Thr | Pro<br>455 |  |

| gcc | agc | aac | atc | acc | ttt | ctc | ccc | ccg | tcg | ctg | aaa | ctc | ctg | aag | tcc | 1853 |
|---|---|---|---|---|---|---|---|---|---|---|---|---|---|---|---|---|
| Ala | Ser | Asn | Ile | Thr<br>460 | Phe | Leu | Pro | Pro | Ser<br>465 | Leu | Lys | Leu | Leu | Lys<br>470 | Ser |  |

| tac | aga | gtt | cta | aaa | tgg | agg | gct | gac | agt | ccc | tcc | atg | aac | tca | agg | 1901 |
|---|---|---|---|---|---|---|---|---|---|---|---|---|---|---|---|---|
| Tyr | Arg | Val | Leu<br>475 | Lys | Trp | Arg | Ala | Asp<br>480 | Ser | Pro | Ser | Met | Asn<br>485 | Ser | Arg |  |

| ttc | tgg | aag | aat | ctt | gtt | tac | ctg | atg | ccc | gca | aaa | gcc | gtc | aag | cca | 1949 |
|---|---|---|---|---|---|---|---|---|---|---|---|---|---|---|---|---|
| Phe<br>490 | Trp | Lys | Asn | Leu | Val<br>495 | Tyr | Leu | Met | Pro | Ala<br>500 | Lys | Ala | Val | Lys | Pro<br>505 |  |

| tgg | aga | gag | gag | tcg | gag | gcg | cgg | tct | gtt | ctc | tca | gca | cct |  | | 1991 |
|---|---|---|---|---|---|---|---|---|---|---|---|---|---|---|---|---|
| Trp | Arg | Glu | Glu | Ser<br>510 | Glu | Ala | Arg | Ser | Val<br>515 | Leu | Ser | Ala | Pro |  |  |  |

| tgagctccag acgagcttga tgtcaaaagc aagtgaagcg ctgctagagg tcatgcgtgt | 2051 |
|---|---|
| gcctattcac agcggtagct gtggttcaaa aggctgaatt ttgtgactat accccccact | 2111 |
| cccagttagg agagttgtca tcgggtcatc acagatgaaa cagagccttg gttgtgatcc | 2171 |

-continued

```
tgaactcgca gagggggcct tgggattcac aagaaatcag tttgttattc tttcttcctc    2231
tggagcagtg attcccaacc tgtgggttgt ggcccctttg gcaaacctttt atctccaaaa   2291 tagatgtacg ctatgattca taactgtagc caactcacag ttacaaagta gcaacgaaaa    2351
aagttttatg gttgggggtt tcaccacagt gtgaagaact gtattaaagg gttgaagcat    2411
taggaaggtt gagaaccgct ggcctagagc tgtctgccca agcttcttg tgaccttgca     2471 agtgcctgag tgaagcaaga atattctagg gaagtctaga gcagagactg tgctgaacaa    2531
acacagtaga ttttaggaaa accaaaccaa accaaatgaa aggaaaggaa acagaaaaaa    2591
aaacaagaag aatggggatt cttaagtaat ttttgtaact catgacttca tgtgctattt    2651
gactgacttg agaaaagaag gtaaattcat tcaacatctg ctgtcacaac agctgtgtgt    2711
gaaaacctag catcagaaga gagttgggag agtttgagac ttcgctttgt tcttctatca    2771
gccaagcttc gacacatgaa gtttatttta tatgaaatat attttgtatt aaatctgcc     2830
```

<210> SEQ ID NO 4
<211> LENGTH: 537
<212> TYPE: PRT
<213> ORGANISM: Homo sapiens

<400> SEQUENCE: 4

```
Met His His Glu Glu Leu Ile Leu Thr Leu Cys Ile Leu Ile Val Lys
        -15                 -10                  -5

Ser Ala Ser Lys Ser Cys Ile His Arg Ser Gln Ile His Val Val Glu
 -1   1              5                  10

Gly Glu Pro Phe Tyr Leu Lys Pro Cys Gly Ile Ser Ala Pro Val His
15                  20                  25                  30

Arg Asn Glu Thr Ala Thr Met Arg Trp Phe Lys Gly Ser Ala Ser His
                35                  40                  45

Glu Tyr Arg Glu Leu Asn Asn Arg Ser Ser Pro Arg Val Thr Phe His
            50                  55                  60

Asp His Thr Leu Glu Phe Trp Pro Val Glu Met Glu Asp Glu Gly Thr
65                  70                  75

Tyr Ile Ser Gln Val Gly Asn Asp Arg Arg Asn Trp Thr Leu Asn Val
        80                  85                  90

Thr Lys Arg Asn Lys His Ser Cys Phe Ser Asp Lys Leu Val Thr Ser
95                  100                 105                 110

Arg Asp Val Glu Val Asn Lys Ser Leu His Ile Thr Cys Lys Asn Pro
                115                 120                 125

Asn Tyr Glu Glu Leu Ile Gln Asp Thr Trp Leu Tyr Lys Asn Cys Lys
            130                 135                 140

Glu Ile Ser Lys Thr Pro Arg Ile Leu Lys Asp Ala Glu Phe Gly Asp
            145                 150                 155

Glu Gly Tyr Tyr Ser Cys Val Phe Ser Val His His Asn Gly Thr Arg
160                 165                 170

Tyr Asn Ile Thr Lys Thr Val Asn Ile Thr Val Ile Glu Gly Arg Ser
175                 180                 185                 190

Lys Val Thr Pro Ala Ile Leu Gly Pro Lys Cys Glu Lys Val Gly Val
                195                 200                 205

Glu Leu Gly Lys Asp Val Glu Leu Asn Cys Ser Ala Ser Leu Asn Lys
            210                 215                 220

Asp Asp Leu Phe Tyr Trp Ser Ile Arg Lys Glu Asp Ser Ser Asp Pro
            225                 230                 235

Asn Val Gln Glu Asp Arg Lys Glu Thr Thr Thr Trp Ile Ser Glu Gly
```

```
                  240                 245                 250
Lys Leu His Ala Ser Lys Ile Leu Arg Phe Gln Lys Ile Thr Glu Asn
255                 260                 265                 270

Tyr Leu Asn Val Leu Tyr Asn Cys Thr Val Ala Asn Glu Glu Ala Ile
                    275                 280                 285

Asp Thr Lys Ser Phe Val Leu Val Arg Lys Glu Ile Pro Asp Ile Pro
                    290                 295                 300

Gly His Val Phe Thr Gly Gly Val Thr Val Leu Val Leu Ala Ser Val
                    305                 310                 315

Ala Ala Val Cys Ile Val Ile Leu Cys Val Ile Tyr Lys Val Asp Leu
                320                 325                 330

Val Leu Phe Tyr Arg Arg Ile Ala Glu Arg Asp Glu Thr Leu Thr Asp
335                 340                 345                 350

Gly Lys Thr Tyr Asp Ala Phe Val Ser Tyr Leu Lys Glu Cys His Pro
                    355                 360                 365

Glu Asn Lys Glu Glu Tyr Thr Phe Ala Val Glu Thr Leu Pro Arg Val
                370                 375                 380

Leu Glu Lys Gln Phe Gly Tyr Lys Leu Cys Ile Phe Glu Arg Asp Val
                385                 390                 395

Val Pro Gly Gly Ala Val Val Glu Glu Ile His Ser Leu Ile Glu Lys
                400                 405                 410

Ser Arg Arg Leu Ile Ile Val Leu Ser Gln Ser Tyr Leu Thr Asn Gly
415                 420                 425                 430

Ala Arg Arg Glu Leu Glu Ser Gly Leu His Glu Ala Leu Val Glu Arg
                    435                 440                 445

Lys Ile Lys Ile Ile Leu Ile Glu Phe Thr Pro Ala Ser Asn Ile Thr
                    450                 455                 460

Phe Leu Pro Pro Ser Leu Lys Leu Leu Lys Ser Tyr Arg Val Leu Lys
                    465                 470                 475

Trp Arg Ala Asp Ser Pro Ser Met Asn Ser Arg Phe Trp Lys Asn Leu
                    480                 485                 490

Val Tyr Leu Met Pro Ala Lys Ala Val Lys Pro Trp Arg Glu Glu Ser
495                 500                 505                 510

Glu Ala Arg Ser Val Leu Ser Ala Pro
                    515

<210> SEQ ID NO 5
<211> LENGTH: 8
<212> TYPE: PRT
<213> ORGANISM: Artificial
<220> FEATURE:
<223> OTHER INFORMATION: FLAG peptide

<400> SEQUENCE: 5

Asp Tyr Lys Asp Asp Asp Asp Lys
1               5
```